(12) United States Patent
Choi et al.

(10) Patent No.: US 11,170,899 B2
(45) Date of Patent: Nov. 9, 2021

(54) BIOMETRIC DATA CAPTURING AND ANALYSIS USING A HYBRID SENSING SYSTEMS

(71) Applicant: Computime Ltd., New Territories (HK)

(72) Inventors: Hung Bun Choi, Hong Kong (CN);
Chun Kit Chu, Hong Kong (CN);
Wai-Leung Ha, Hong Kong (CN);
Leung Yin Chan, Hong Kong (CN)

(73) Assignee: Computime Ltd., New Territories (HK)

( * ) Notice: Subject to any disclaimer, the term of this patent is extended or adjusted under 35 U.S.C. 154(b) by 20 days.

(21) Appl. No.: 16/797,071

(22) Filed: Feb. 21, 2020

(65) Prior Publication Data

US 2020/0194127 A1 Jun. 18, 2020

Related U.S. Application Data

(63) Continuation-in-part of application No. 16/559,814, filed on Sep. 4, 2019, now Pat. No. 10,943,137.
(Continued)

(51) Int. Cl.
*G16H 50/30* (2018.01)
*G16H 10/60* (2018.01)
(Continued)

(52) U.S. Cl.
CPC ........... *G16H 50/30* (2018.01); *G06N 3/0454* (2013.01); *G06N 3/08* (2013.01); *G16H 10/60* (2018.01)

(58) Field of Classification Search
CPC ........... G06K 9/00845; G06K 9/00369; B60N 2/002; B60W 40/08; B60W 2040/0809;
(Continued)

(56) References Cited

U.S. PATENT DOCUMENTS

| 10,007,263 B1* | 6/2018 | Fields ................. B60W 30/09 |
| 2003/0214408 A1* | 11/2003 | Grajales ............... G08B 21/02 |
| | | 340/573.1 |

(Continued)

FOREIGN PATENT DOCUMENTS

| WO | 2018/201688 A1 | 11/2018 |
| WO | 2019/081975 A1 | 5/2019 |

(Continued)

OTHER PUBLICATIONS

Nov. 27, 2020—(WO) International Search Report and Written Opinion application PCT/US20/49127.
(Continued)

*Primary Examiner* — Omar Casillashernandez
(74) *Attorney, Agent, or Firm* — Banner & Witcoff, Ltd.

(57) ABSTRACT

Apparatuses and methods detect a health condition of a user that may be assessed from a thermal sensor signal and/or radar sensor signal. One or more resultant biometric vectors may be generated from biometric vectors based on the thermal and radar signals, where the resultant biometric vectors contain resultant information about one or more biometric features for a user. Hazard information about the user is obtained from the one or more resultant biometric vectors, where the hazard information is indicative of a health event for the user. Consequently, an appropriate action on behalf of the user may be performed to ameliorate the health condition. The one or more resultant biometric vectors may include additional biometric features and/or a time sequence of the resultant biometric vectors to enhance hazard prediction. Moreover, the apparatuses and methods may support the user in different settings including a home, business, or vehicle.

27 Claims, 18 Drawing Sheets

Related U.S. Application Data

(60) Provisional application No. 62/730,160, filed on Sep. 12, 2018.

(51) Int. Cl.
  G06N 3/08 (2006.01)
  G06N 3/04 (2006.01)

(58) Field of Classification Search
  CPC .. B60W 2040/0818; B60W 2040/0881; G05D 1/0061; G06F 21/32; H04L 9/3231
  USPC ......................................................... 340/576
  See application file for complete search history.

(56) References Cited

U.S. PATENT DOCUMENTS

| | | | |
|---|---|---|---|
| 2009/0119047 A1* | 5/2009 | Zelin | G01N 27/3274 |
| | | | 702/82 |
| 2012/0095358 A1 | 4/2012 | Matsunaga et al. | |
| 2013/0173926 A1 | 7/2013 | Morese et al. | |
| 2013/0314536 A1 | 11/2013 | Frank et al. | |
| 2014/0276090 A1 | 9/2014 | Breed | |
| 2015/0094914 A1* | 4/2015 | Abreu | B60H 1/00742 |
| | | | 701/41 |
| 2016/0152180 A1* | 6/2016 | Kirsch | B60Q 1/50 |
| | | | 701/36 |
| 2017/0095157 A1* | 4/2017 | Tzvieli | A61B 5/0077 |
| 2017/0124853 A1* | 5/2017 | Mehta | G08B 25/009 |
| 2017/0249433 A1 | 8/2017 | Hagen et al. | |
| 2017/0374065 A1* | 12/2017 | Shtraym | G06K 9/6202 |
| 2018/0082037 A1* | 3/2018 | Arbouzov | G16H 40/67 |
| 2018/0114329 A1 | 4/2018 | Wexler et al. | |
| 2019/0099290 A1* | 4/2019 | Thomas | A61F 7/08 |
| 2020/0082189 A1* | 3/2020 | Choi | B60W 40/08 |
| 2020/0194127 A1* | 6/2020 | Choi | G06N 3/08 |

FOREIGN PATENT DOCUMENTS

| | | | | |
|---|---|---|---|---|
| WO | 2019/103620 A2 | 5/2019 | | |
| WO | WO-2019081975 A1 * | 5/2019 | ........... | H04L 9/3231 |

OTHER PUBLICATIONS

Mar. 6, 2020—International Search Report & Written Opinion—PCT/US2019/049666.

* cited by examiner

BIOMETRIC DATA CAPTURING AND ANALYSIS USING A HYBRID SENSING SYSTEMS

This patent application is a continuation-in-part to U.S. Non-Provisional application Ser. No. 16/559,814, filed Sep. 4, 2019 which claims priority to U.S. provisional patent application Ser. No. 62/730,160 entitled "Biometric Data Capturing and Analysis" filed on Sep. 12, 2018, which is hereby incorporated by reference in its entirety.

TECHNICAL FIELD

Aspects of the disclosure relate to extracting biometric data from thermal and radio frequency (RF) sensors and to perform an appropriate action.

BACKGROUND OF THE INVENTION

Image sensors are popular for home applications. Examples include those used for a baby monitor, internet protocol (IP) camera, security camera, and so. Other image sensors include thermal cameras as well as an array of thermal sensors. Expanding the effective applications of image sensors would enhance the popularity.

The need to expand the application of sensors (for example, thermal sensors) is underscored by an article reported in the Chicago Sun Times in May 2019 about an Illinois man who died after suffering a heart-related event while driving and crashing his vehicle. The man was driving when he suffered a "heart-related event," lost consciousness, and crashed his vehicle into a utility pole. After crashing into the pole, his car struck another vehicle. Preventive measures addressing such horrific events would certainly be beneficial to the general population.

SUMMARY OF THE INVENTION

An apparatus detects a health condition of a user that may be assessed from a thermal sensor signal and/or radar sensor signal. One or more resultant biometric vectors may be generated from biometric vectors based on the thermal and radar signals, where the resultant biometric vectors contain resultant information about one or more biometric features associated with a user.

With another aspect, hazard information about a user is obtained from the one or more resultant biometric vectors, where the hazard information is indicative of a health event associated with the user. Consequently, an appropriate action on behalf of the user may be performed to ameliorate the health condition. The one or more resultant biometric vectors may include additional biometric features and/or a time sequence of the resultant biometric vectors to enhance hazard prediction.

With another aspect, when a thermal signal is not available, resultant information about the first biometric feature is extracted only from information contained the second biometric vector from the radar signal.

With another aspect, a thermal signature, which identifies a user, is extracted from a thermal signal. When a health event is detected, an apparatus sends a message indicative of the hazard level about the user to a medical facility.

With another aspect, an apparatus downloads a health record of a user. Biometric features may be weighed differently based on the health record.

With another aspect, first and second trained machine learning models may transform thermal signals and radar signals, respectively. The transformed signals are then used to obtain biometric vectors. Moreover, a thermal signature and/or motion vector provided by the first machine learning model to the second machine learning model may assist in transforming the radar signal.

With another aspect, machine learning models may be downloaded by an apparatus from a cloud server. The models may be updated at the cloud server so that updated model information can be received by the apparatus in order to update the downloaded models.

With another aspect, an apparatus provides an assessment of a vehicle driver. The apparatus obtains a thermal signal and a radar signal about the vehicle driver from a thermal sensor and a radar sensor, respectively. The apparatus generates biometric vectors from the thermal and radar signals, extracts resultant information about one or more biometric features, and generates a resultant biometric vector from the resultant information. The apparatus then determines hazard information from the resultant biometric vector when a health event occurs. Based on the hazard information, the apparatus identifies an appropriate action and performs the appropriate action on behalf of the vehicle driver.

With another aspect, an apparatus downloads a chronicle health record and conduct record of a vehicle driver and identifies an appropriate action based on the chronicle health and conduct record.

With another aspect, an apparatus applies a first weight to the first resultant information about a first biometric feature and a second weight to a second resultant information about a second biometric feature based on the chronicle health and conduct record of a vehicle driver.

With another aspect, when a health event about a vehicle driver is detected, an apparatus sends a chronicle health and conduct record to an emergency service to prepare for the arrival of the vehicle driver.

With another aspect, an apparatus uses a thermal sensor for biometric data extraction and tracking for smart home applications. Applications such as health condition analysis, motion estimation (for example, fall estimation or motion trajectory), casual prediction (for example, heart beat is slowing down to a hazardous level), hazard detection (for example, endurance abnormal body position such as laying down on floor, laying sideway on sofa or head down for a long time), learning the profile of individuals, and system adaptation according to individual preferences.

With another aspect, parameters of a thermal sensor may be enhanced to allow as much data to be extracted as possible. Examples include, but not limited to: increasing the number of sensing element (i.e., the resolution), frame rate, sensitivity, and/or signal-to-noise level.

With another aspect, signal processing techniques extract biometric data from the thermal images.

With another aspect, an analytic model is used for hazard prediction and subsequently associated actions taken.

With another aspect, hazard analysis is done by a deep learning model. Actions are taking based on the hazard coefficients with the associated confidence levels estimated from the model.

With another aspect, the model would suggest actions to be taken with the associated confidence levels based on the input data sequence.

With another aspect, the model may be trained to predict the hazard coefficients, and the corresponding actions if necessary, with the corresponding confidence levels based on the events previously occurring.

With another aspect, the model may reside in a cloud server rather than a local processing unit for applications that are less time critical.

With another aspect, parameters of a smart device are configured differently based on a thermal signature of a detected person.

With another aspect, an executed application is changed from a first application to a second application based on a detected condition detected by the first application.

BRIEF DESCRIPTION OF THE DRAWINGS

The foregoing summary of the invention, as well as the following detailed description of exemplary embodiments of the invention, is better understood when read in conjunction with the accompanying drawings, which are included by way of example, and not by way of limitation with regard to the claimed invention.

DETAILED DESCRIPTION

Figure 1:
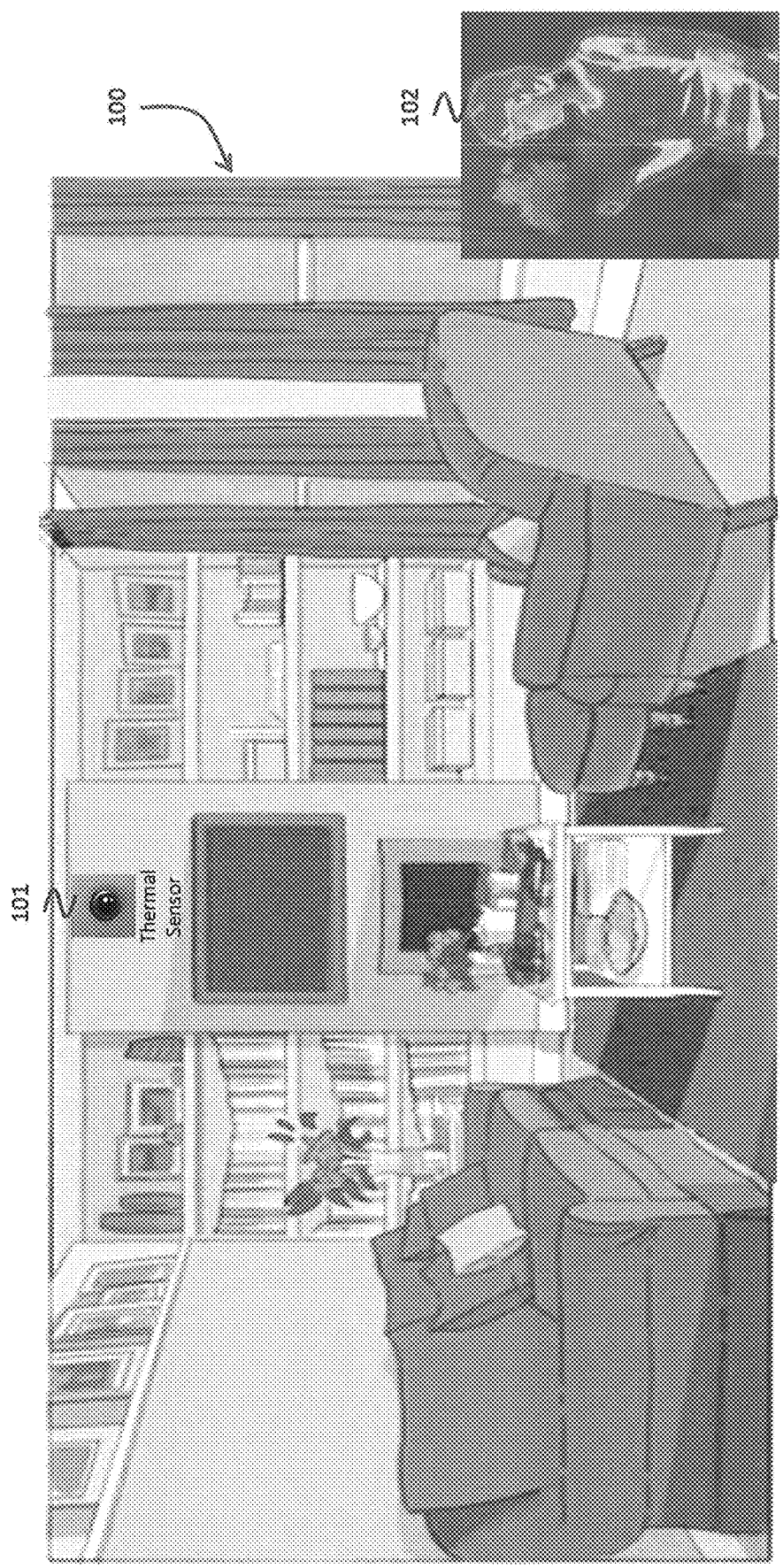
FIG. 1 shows a thermal sensor positioned in a room in accordance with an embodiment.

According to an aspect of the embodiments, an apparatus detects a health condition of a user that may be assessed from a thermal sensor signal and/or radar sensor signal. One or more resultant biometric vectors may be generated from biometric vectors based on the thermal and radar signals, where the resultant biometric vectors contain resultant information about one or more biometric features for a user. Hazard information about the user is obtained from the one or more resultant biometric vectors, where the hazard information is indicative of a health event for the user. Consequently, an appropriate action on behalf of the user may be performed to ameliorate the health condition. The one or more resultant biometric vectors may include additional biometric features and/or a time sequence of the resultant biometric vectors to enhance hazard prediction.

With another aspect of the embodiment, performance indices (for example, resolution, frame rate, and sensitivity) of a thermal sensor or an array of thermal sensors may be increased to support applications such as identification verification, biometric data extraction, and health condition analysis. Prediction may be carried out by monitoring a time sequence of thermal images and consequently an early warning of the health condition may be generated.

With another aspect of the embodiments, the frame rate of a thermal sensor may be increased to a determined level to capture the change in the minor details in the thermal radiation from a human body against time, for example, the detail change in the thermal radiation from human body.

With another aspect of the embodiments, the thermal image of the blood flows through the skin may be converted to a time signal for pulse rate extraction. Further signal processing techniques may be applied to extra biometric data of an individual for analyzing the health condition. An image signal may be processed to identify multiple objects from the content and to track associated biometric data.

With another aspect of the embodiments, an application may determine the position of a human body within the image signal, together with motion tracking from the previous images, for fall detection. Motion estimation may be applied to predict if there is any hazard to the individuals within the image signal.

With another aspect of the embodiments, a profile may be associated to an individual. An apparatus may track and learn the behavior of the individual from the history of image signal. Moreover, the apparatus may adapt when the individual is detected in the scene. For example, the set temperature of the air conditioner in the sitting room may be adapted to an individual's preference when the individual is detected going into the sitting room in the summer time.

With another aspect of the embodiments, the environment temperature can be controlled according to the body surface temperature of individual(s), together with other parameters (such as relative humidity and outside temperature, and so forth) to reach the overall comfort zone through machine learning.

With another aspect of the embodiments, the accuracy of an analysis is determined by the resolution, sampling frequency and sensitivity of a thermal sensor, signal processing techniques in extracting biometric data from the image signals, and analytic/learning algorithms.

With another aspect of the embodiments, applications of thermal sensors may be extended to domestic applications.

With another aspect of the embodiments, the analytic model is composed of a trained model.

The model is trained from a database of reference thermal image signals and an associated target vector, which may represent a series of settings for the smart home devices. Reinforcement learning may be deployed to allow the model to adapt to a new target vector. For example, a user may change the temperature setting of a room between summer and winter.

With another aspect of the embodiments, no training is applied to the analytic model but learning from the sequence of target vectors over time that is associated with a thermal signature. For example when a new thermal signature, which is associated with a new user, is detected, a default setting for the smart him devices is applied. When the user changes the setting of individual device, the new setting would be recorded for re-training the model.

FIG. 1 shows thermal camera 101 positioned in room 100 in accordance with an embodiment. Camera 101 may generate thermal image (thermogram) 102 of an individual not explicitly shown.

With some embodiments, thermal camera 101 comprises a lens that focuses infrared or far-infrared radiation by objects in view. The focused light is scanned by a thermal sensor, which comprises a plurality of infrared-detector elements (for example, 24 by 32 pixels). The detector elements may create a very detailed temperature pattern (for example, thermogram 102).

With some embodiments, camera 101 may require one-hundredth of a second for the detector array to obtain sensor information to obtain the thermal image. The sensor information may be periodically obtained from several thousand points in the field of view of the thermal sensor to form a sequence of thermal images.

Thermogram 102 created by the detector elements of the thermal sensor may be converted into electric impulses. The impulses are then sent to a signal-processing unit (for example, apparatus 300 as shown in FIG. 3), which may be implemented as a circuit board with a dedicated chip that converts the sensor information into biometric data.

Thermal camera 101 may also include a tracking capability so that the direction of camera 101 may vary to track a moving object such as person 102 moving in room 100.

While FIG. 1 depicts one thermal sensor, some embodiments may interface with a plurality of thermal sensors. For example, thermal sensor arrays may be positioned in different rooms and/or at entry points of a dwelling.

Figure 2:
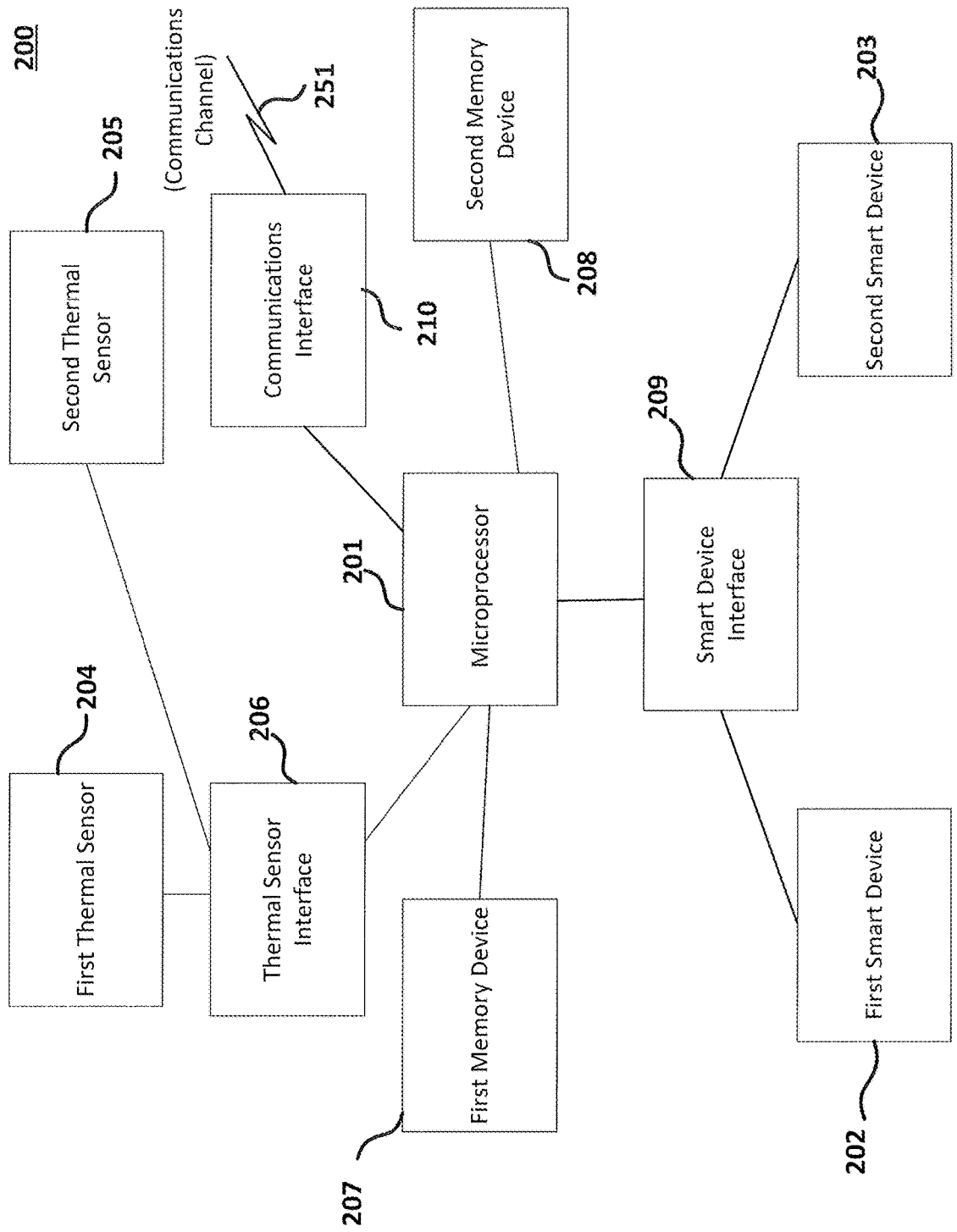
FIG. 2 shows an apparatus interfacing with one or more thermal sensors and one or more associated smart devices in accordance with an embodiment.

FIG. 2 shows apparatus 200 interfacing with thermal sensor 204 and/or 205 through sensor interface 206 and smart devices 202 and/or 203 through smart device interface 209 in accordance with an embodiment.

Thermal sensors 204 and 205 are often used for access control and presence detection. With some embodiments, in order for processor 201 to extract biometric data from sensor information, the performance of thermal sensor 204 may be extended by increasing the sample frequency (for example, frame rate) of capturing the image signal, identifying and tracking individuals from the image signal, and analyzing detail changes in thermal images against time. Processor 201 may convert sensor information (signals) to biometric data, such as heart rate, body position, health condition, and so forth. Apparatus 200 may also support prediction of future health events may by processing the image signals and/or support system personalization.

With some embodiments, processor 201 may process sensor information to detect a thermal signature of a user. When a thermal signature of a particular individual is detected, processor 201 may apply the individual's profile (for example, a temperature setting) to smart device 202 (for example, an air conditioner).

Processor 201 may support one or more health applications that processes and/or analyzes biometric data and may generate notifications about the biometric data to an external entity (for example, a doctor) over communications channel 251 via interface 210. As an example, a health application may detect that a user is having a possible heart attack from the biometric data; consequently, an urgent notification is sent to the user's doctor about the event.

With reference to FIG. 2, a computing system environment may include a computing device where the processes (for example, process 300 shown in FIG. 3) discussed herein may be implemented. The computing device may include processor 201 for controlling overall operation of the computing device and its associated components, including RAM, ROM, communications module, and first memory device 207. The computing device typically includes a variety of computer readable media. Computer readable media may be any available media that may be accessed by computing device and include both volatile and nonvolatile media, removable and non-removable media. By way of example, and not limitation, computer readable media may comprise a combination of computer storage media and communication media.

Computer storage media may include volatile and nonvolatile, removable and non-removable media implemented in any method or technology for storage of information such as computer readable instructions, data structures, program modules or other data. Computer storage media include, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by the computing device.

Communication media typically embodies computer readable instructions, data structures, program modules or other data in a modulated data signal such as a carrier wave or other transport mechanism and includes any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

With some embodiments, processor 201 may execute computer-executable instructions stored at memory 207 and access profile data stored at memory 208.

With some embodiments, memory devices 207 and 208 may be physically implemented within a single memory device.

Figure 3A:
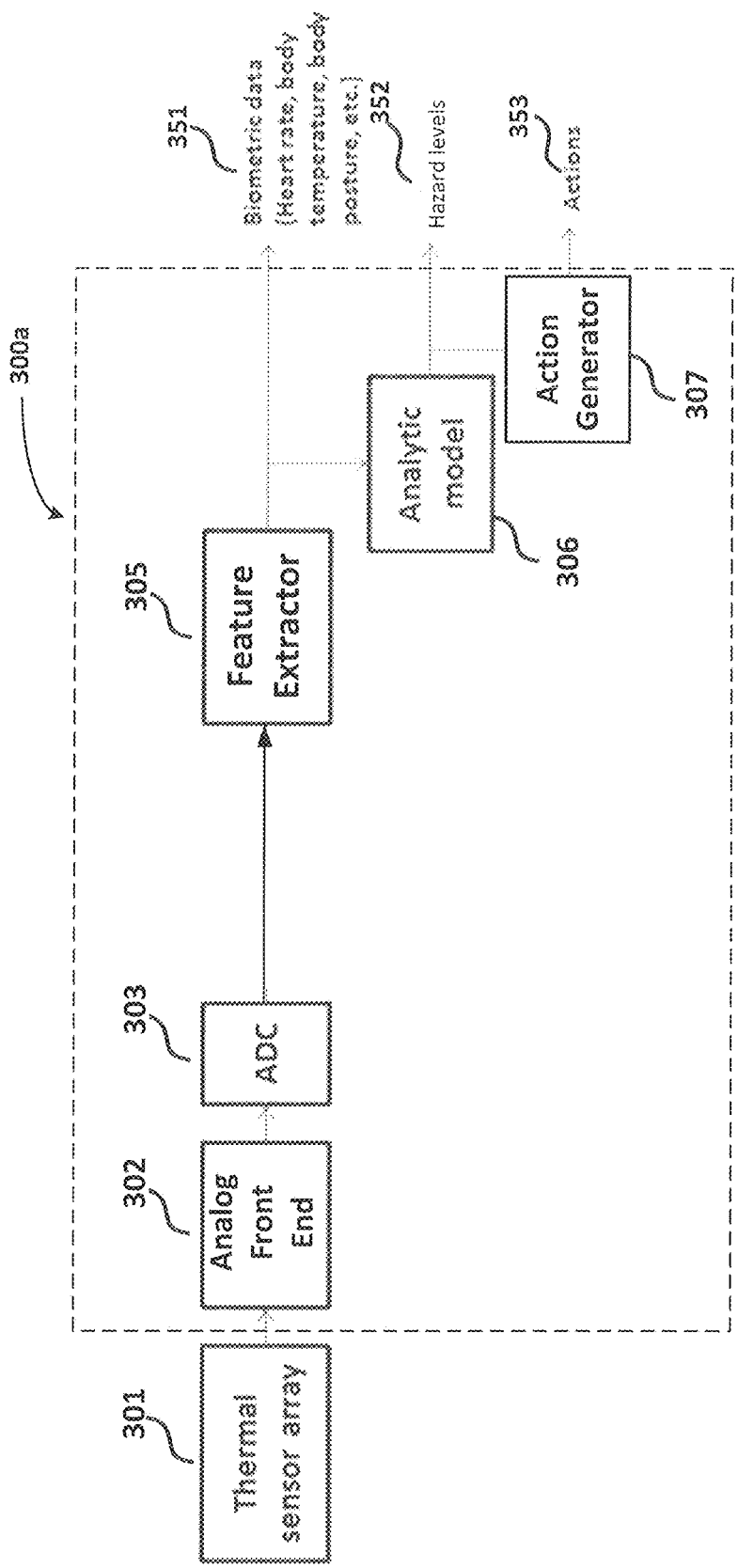
FIG. 3*a* shows an apparatus that processes information from one or more thermal sensors in accordance with an embodiment.

FIG. 3a shows apparatus 300a that processes information from one or more thermal sensors 301 in accordance with an embodiment.

By using a higher quality thermal sensor 301 (for example, with a frame rate of at least 100 frames per second, resolution of at least 24×32 pixels, good sensitivity, and low noise), biometric data 351 may be extracted via appropriate signal processing techniques via analog front end 302, analog to digital convertor (ADC) 303, and feature extractor 305. Biometric data 351 may include pulse rate, body surface temperature, temperature distribution pattern, body contour and posture, and so forth. By tracking the variations of biometric data, the health condition of an individual may be analyzed by analyzer 306, and early warning signals 352 and 353 may be generated by analyzer 306 and action generator 307, respectively, by further processing biometric data 351.

An application may utilize a domestic thermal camera installed for fall detection by tracking the change of posture. For example, when the posture changes from upright to horizontal in a short time, a possible fall may be detected and hence an associated alert may be generated. Moreover, a variation of posture, body surface temperature, temperature distribution pattern, and heart rate may be tracked to estimate the hazard level, and associated actions 353 can be taken.

Hazard prediction from biometric data 351 may also supported. For example, when one's body surface temperature is continuously dropping and his/her posture is shaking, the chance of a fall may be higher (as indicated by hazard level 352) and hence an alert may be generated (triggered) before a fall can occur.

Block 302 may perform signal amplification and non-recursive band-pass filtering, in which the analog signal corresponding to the thermal image is processed for DC offset removal, noise reduction and frequency limited before being processed by ADC 303. (With some embodiments, block 303 may comprise a 16-bit ADC with the sampling frequency (for example, 200 Hz) being set high enough to capture the details of temperature change of an object.)

In the feature extraction block 305, image processing is applied to identify valid objects, track the thermal profile of individual objects over time and extract the parameters from the thermal profile to form a feature vector. Examples of the parameters for the feature vector include period time, variation of the period times, certain time constants within each periodic cycle and their variations over time, etc. The analytic model 306 takes in the feature vector and compares it over a trained model. The model is pre-trained with a large set of generic feature vectors using deep learning algorithms, e.g. a deep neural network. Reinforcement learning may be deployed to allow the model to learn from the mistakes. Hazard levels may be provided for the identified objects. In block 307, a list of actions may be pre-defined and may be triggered based on the associated hazard levels.

Figure 3B:
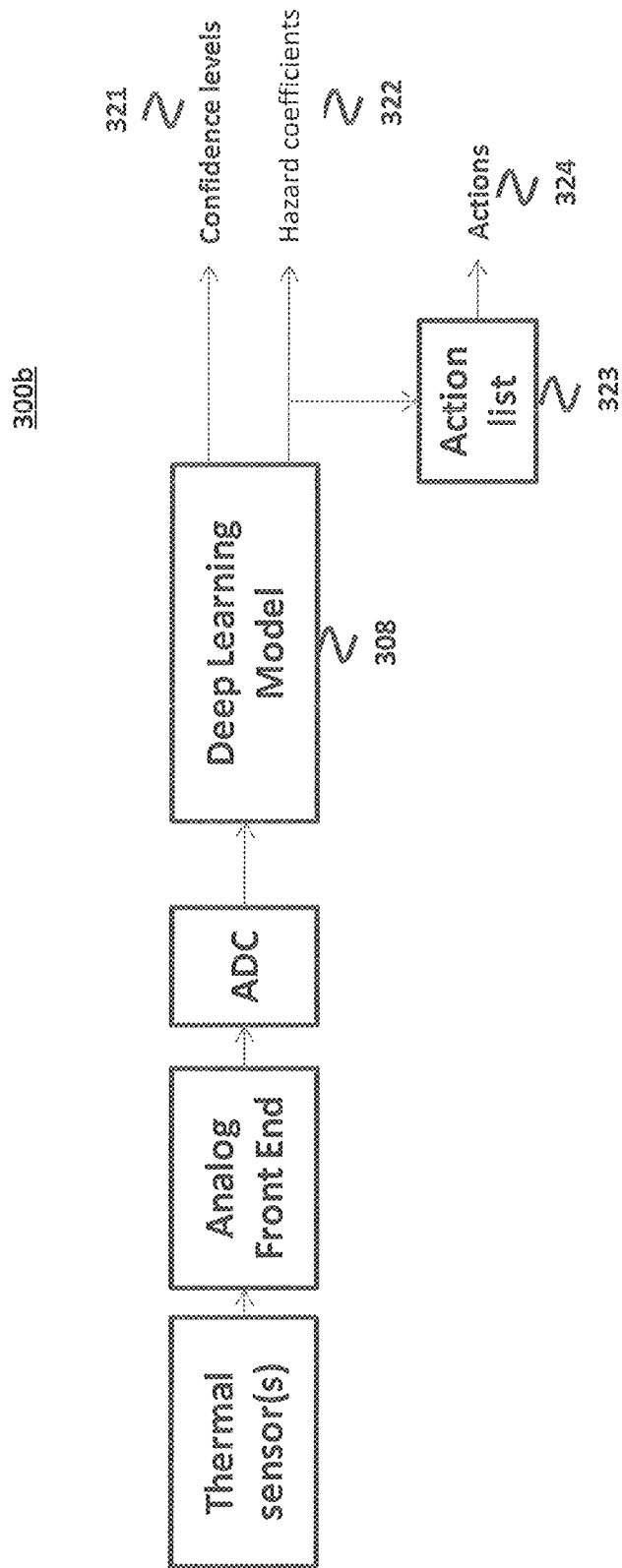
FIG. 3*b* shows an apparatus that processes information from one or more thermal sensors in accordance with another embodiment using a deep learning model to estimate the hazard coefficients.

FIG. 3b shows apparatus 300b that processes information from one or more thermal sensors 301 in accordance with another embodiment. Hazard coefficients 322 with associated confidence levels 321 are estimated by a model trained using a deep learning model 308, for example, a convolutional neural network with supervised learning. Actions 324 are determined from action list 323 and may be based on hazard coefficients 322 and confidence level 321 provided by model 308. Model 308 may initially support hazard levels but subsequently identify different hazards with more empirical data such as heart-rate abnormality, body surface temperature drop, fall detection, and so forth.

Model 308 in apparatus 300b may also be trained to predict hazards, rather than estimating hazards, based on the training sequence which started from a substantially earlier time.

Figure 3C:
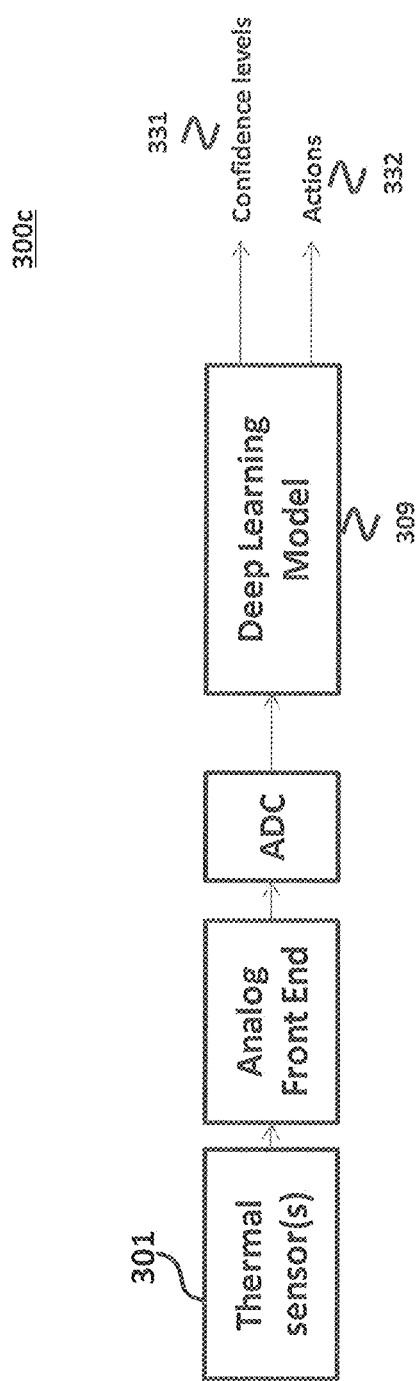
FIG. 3*c* shows an apparatus that processes information from one or more thermal sensors in accordance with another embodiment using a deep learning model to suggest the actions.

FIG. 3c shows apparatus 300c that processes information from one or more thermal sensors 301 in accordance with a third embodiment, in which actions 332 and associated confidence levels 331 are estimated by trained model 309. Again, model 309 in apparatus 300c also may be trained to predict any actions needed.

The image processing technique that may be used depends on the system complexity, including the number of thermal sensors, the resolution of each thermal sensor, the list of hazards and actions, the system computation power and memory available, and so forth.

For the embodiments shown in FIGS. 3a, 3b and 3c, the analytic models may be implemented locally or in a cloud server, depending on criticality of response time.

Figure 4:
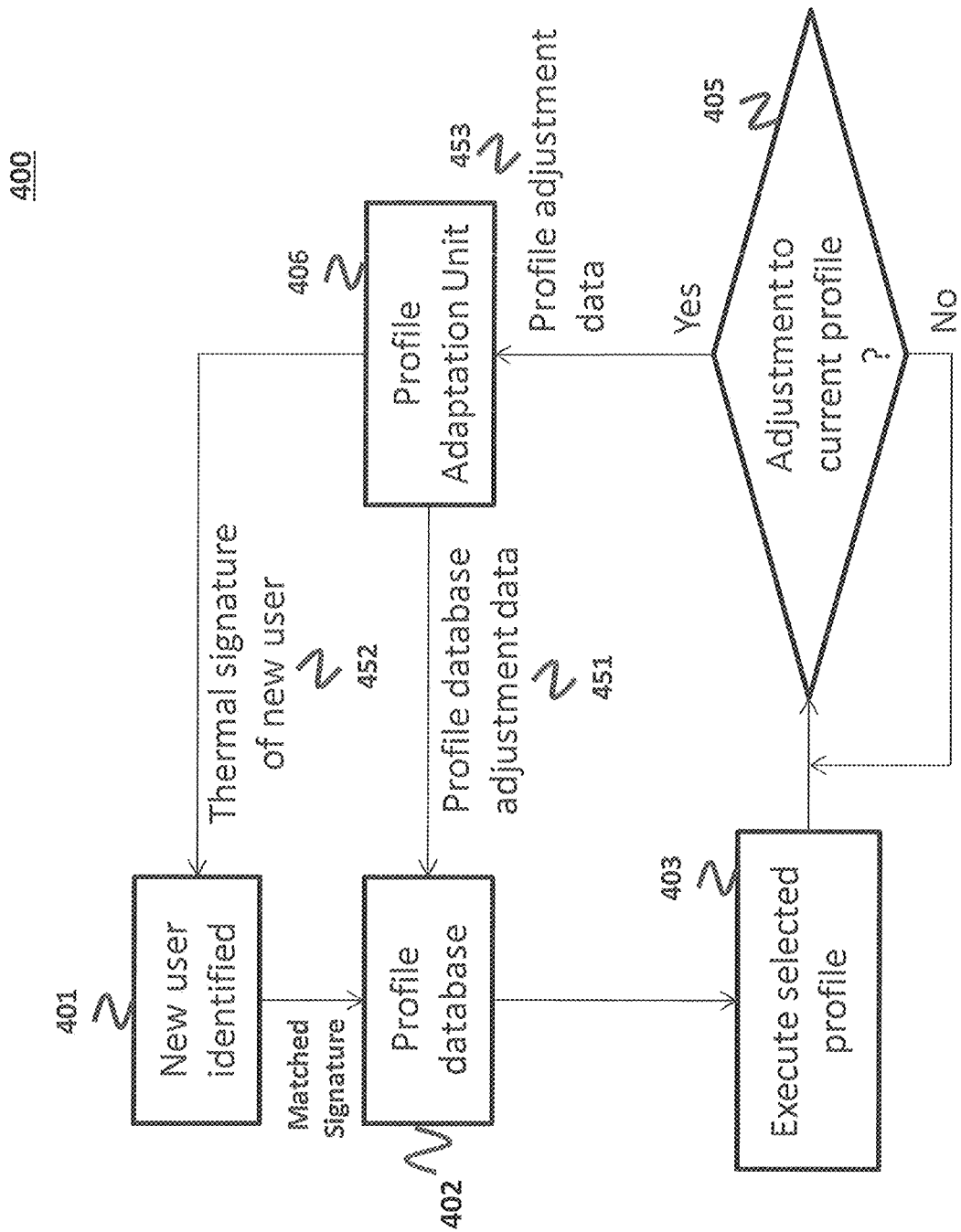
FIG. 4 shows a process that identifies a user from thermal sensor information and applies a corresponding profile in accordance with an embodiment.

FIG. 4 shows process 400 that identifies a user from thermal sensor information and applies a corresponding profile in accordance with an embodiment.

Process (application) 400 supports human presence detection and thermal signature verification at block 401. If a human object is detected and the thermal signature is matched to a known entity at block 401, all supported smart devices (for example, air conditioner, smart TV, or smart lighting) may be adjusted 403 in accordance with the profile database stored at block 402.

If there is any adjustment to the applied profile 405, the adjustment data 453 may be sent to a profile adaptation unit 406 in which the new settings in the profile may be included. The profile database would be updated 451 by profile adaptation unit 406 if an adjustment is needed.

To add a new user, profile adaptation unit 406 sends the thermal signature of the new user 453 to the user identifier unit 401 together with the associated profile, which could be a default profile, to the profile database unit 402.

Profile adaptation unit 406 may comprise a deep learning model trained using reinforcement learning.

Figure 5:
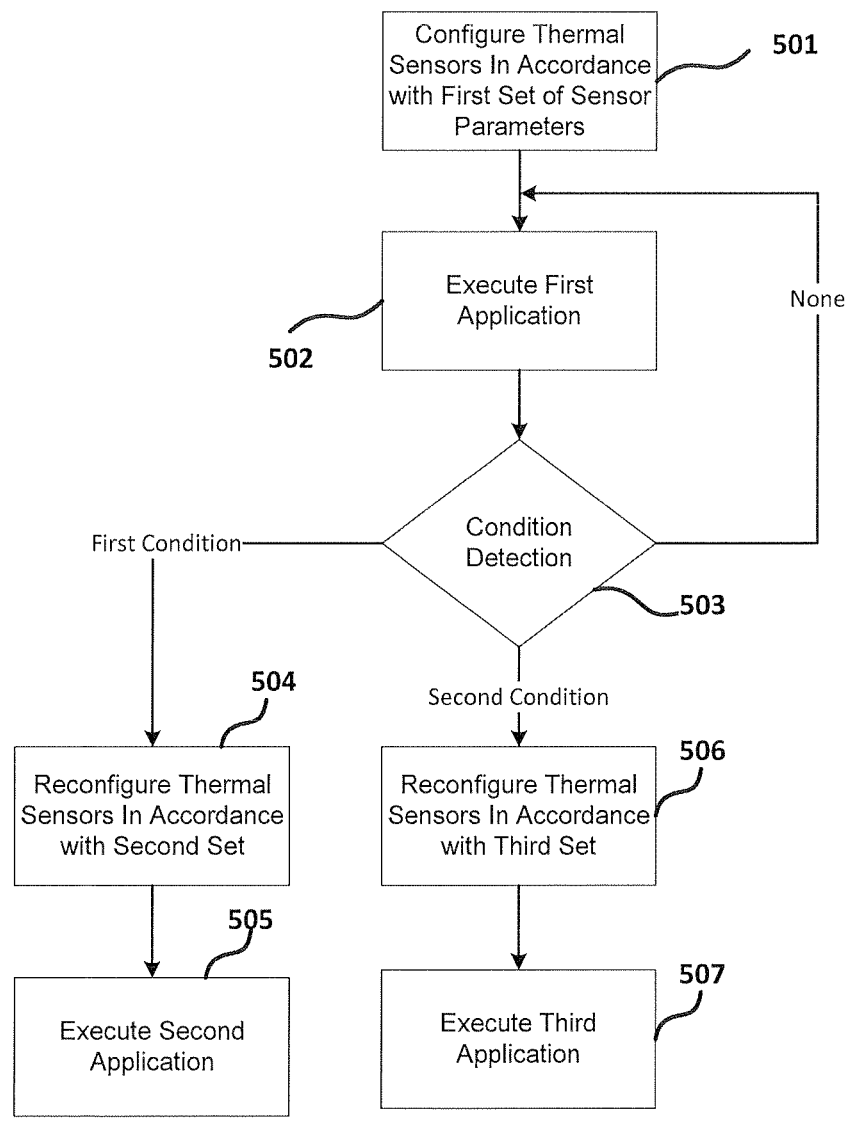
FIG. 5 shows a flowchart for executing a plurality of applications in accordance with an embodiment.

FIG. 5 shows flowchart 500 for sequencing through a plurality of applications, as executed by apparatus 200, in accordance with an embodiment. Apparatus 200 may execute one of the plurality of applications depending on a detected condition. For example, a first health application may monitor general health measurements (for example, an amount of activity and temperature) of a user. If one or more of the measurements are abnormal, apparatus 200 may initiate different health applications based on the detected condition.

Referring to FIG. 5, apparatus 200 configures thermal sensors 204 and 205 in accordance with a first set of sensor parameters at block 501 in order to execute a first application at block 502.

If an abnormal condition is detected at block 503, apparatus 200 initiates an appropriate application. For example, apparatus may transition to a second application to monitor fall prediction or to a third application to monitor the heart rate of the user at blocks 504-505 and 506-507, respectively. When executing the second or third applications, apparatus 200 may configure thermal sensors 204 and 205 differently in order to obtain different biometric data.

In another implementation, different configuration parameters may be applied to individual sensor for each application.

In a third implementation, different sets of configuration parameters are applied to the sensors one after another to extract all the biometric data before running the applications.

In a fourth implementation, a most comprehensive set of configuration parameters is used for all sensors and applications. All of the sensors may be set to the best set of configuration, for example but no limited to, highest image resolution, number of bits, frame rate, sensitivity, signal to noise ratio (SNR), computational power, power consumption, and so forth.

Figure 6:
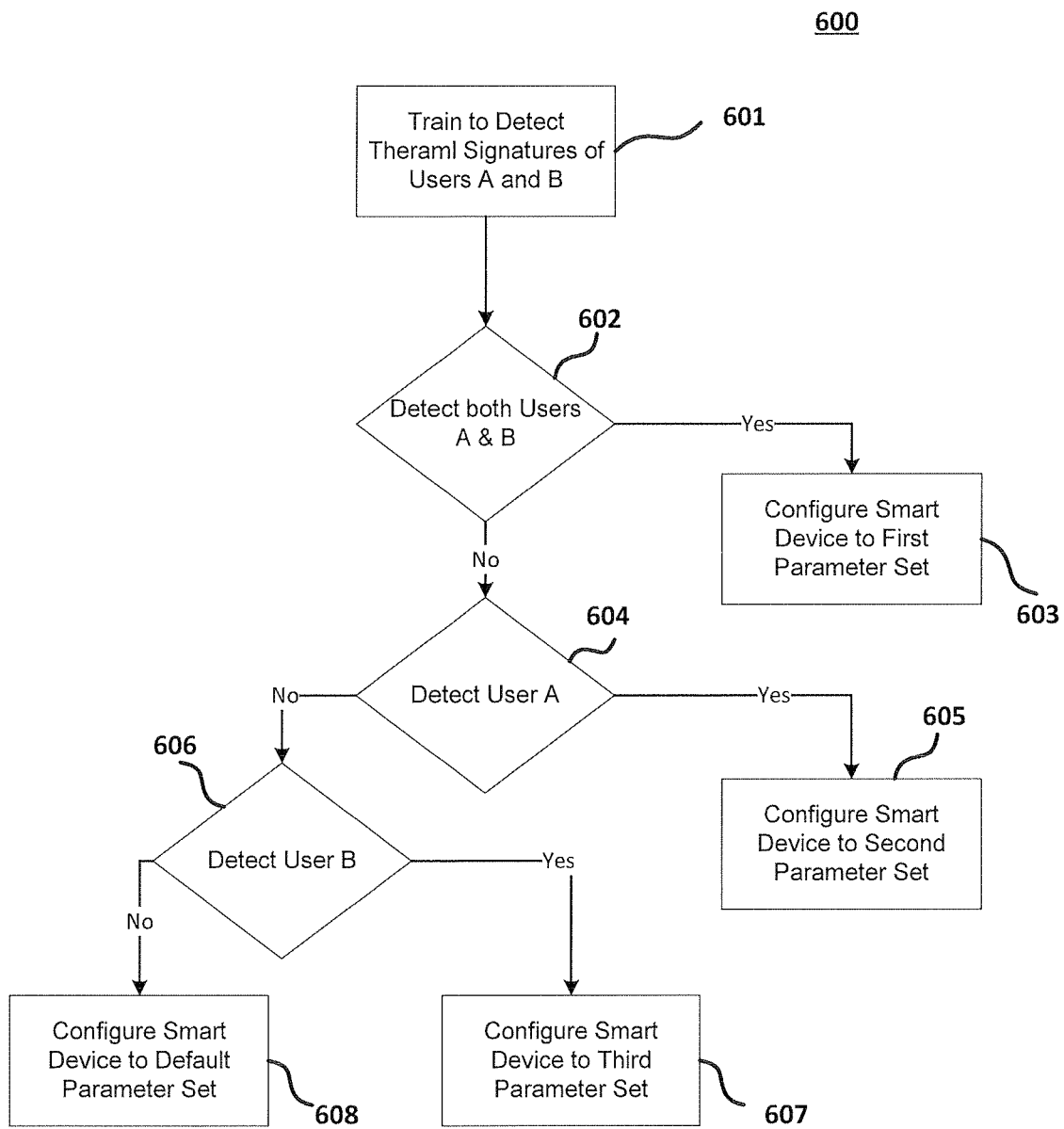
FIG. 6 shows a flowchart for configuring a smart device with one of a plurality of parameter sets based on detected thermal signatures in accordance with an embodiment.

FIG. 6 shows flowchart 600 where apparatus 200 configures a smart device with one of a plurality of parameter sets based on detected users in accordance with an embodiment. Apparatus 200 may monitor sensor data from thermal sensors 204 and/or 205 to detect thermal signatures of one or more users. For example, thermal sensor 204 may be positioned at an entry point of a dwelling. Based on sensor information obtained from sensor 204, apparatus 200 may identify users entering and exiting the dwelling. With some embodiments, apparatus may detect either a thermal signature from the front (corresponding to a person entering the dwelling) or from the back (corresponding to the person exiting the dwelling). Based on the detected thermal signatures, a smart device can be configured with different sets of parameters (for example, the temperature setting of an air conditioner).

At block 601, apparatus 200 trains to detect thermal signatures of different users from sensor data. For example distinguishing characteristics may be stored at memory 208. When thermal signatures of both users are detected at block 602, only user A at block 604, or only user B at block 606, a smart device may be configured in accordance with a first set of smart device parameters at block 603, a second set at block 605, or a third set at block 607, respectively. With some embodiments, the first set (when both users are detected) may be a compromise between the second and third sets (when only one user is detected). Otherwise (when no users are detected), the smart device may be configured in accordance with a default set of smart device parameters at block 608.

The following capabilities may be supported by the embodiments.

An apparatus uses a thermal sensor for biometric data extraction and tracking for smart home applications. Applications such as health condition analysis, motion estimation (for example, fall estimation), casual prediction (for example, heart beat is slowing down to hazard level), hazard detection (for example, laying down for a long time), learning the profile of individuals, and system adaptation according to individual preferences.

The parameters of a thermal sensor may be enhanced to allow as much data to be extracted as possible. Examples include, but not limited to:

a. Increasing the resolution, frame rate, sensitivity and signal-to-noise level, for example, for heart rate monitoring.

b. Increasing the resolution, sensitivity and signal-to-noise level, and so forth for detection distance.

c. Increasing the resolution for the number of tracked objects.

Signal processing techniques extract biometric data from thermal images.

Analytic model for hazards estimation and subsequently the associated actions taken.

Analytic model for actions estimation.

Analytic model for hazards and/or actions prediction.

Model for learning the behaviors of individual(s) to the smart devices according to the biometric data extracted from the thermal sensors.

Configure parameters of a smart device based on different detected people.

Change to a second health application from a first health application based on a detected condition by the first health application. The set of configuration parameters for individual sensors for an active health application may or may not be identical.

Use different set of configuration parameters to extract all biometric data before running the health applications.

Using a single comprehensive set of configuration parameters for all the sensors and health applications.

Obtain thermal sensor data to detect a thermal signature for either the front or the back of a person.

Able to increase the sampling frequency of thermal sensors, including IP cameras, thermal cameras, and thermal sensors, to capture the minor changes of the color content due to thermal radiation from a human body.

Able to increase the resolution and sensitivity of thermal sensors to span the detection range.

Exemplary Clauses

1. An apparatus supporting at least one smart device, the apparatus comprising:
   a smart device interface;
   a thermal sensor interface configured to obtain sensor information from a first thermal sensor;
   a processor for executing computer-executable instructions;
   a memory storing the computer-executable instructions that when executed by the processor cause the apparatus to perform:
     detecting, from the sensor information, a detected thermal signature of a detected user;
     when the detected user is a first user, obtaining a first profile corresponding to the first user, wherein the first profile comprises a first set of smart device parameters; and
     when the detected user is the first user, configuring, through the smart device interface, a first smart device based on the first set of smart device parameters.

2. The apparatus of clause 1, wherein the memory storing computer-executable instructions that when executed by the processor further cause the apparatus to perform:
   when the detected user is a second user, obtaining a second profile corresponding to the second user, wherein the second profile comprises a second set of smart device parameters and wherein the second set is different from the first set; and
   when the detected user is the second user, configuring, through the smart device interface, the first smart device based on the second set of smart device parameters.

3. An apparatus supporting at least one smart application, the apparatus comprising:
   a thermal sensor interface configured to obtain sensor information from a first thermal sensor;
   a processor for executing computer-executable instructions;
   a memory storing the computer-executable instructions that when executed by the processor cause the apparatus to perform:
     when executing a first application:
       configuring the thermal sensor in accordance with a first set of sensor parameters;
       when the thermal sensor is configured with the first set of parameters, extracting biometric data from the sensor information; and
       when a first condition is detected from the biometric data, initiating a second application; and
     when executing the second application,
       configuring the thermal sensor in accordance with a second set of parameters, wherein the first and second sets differ by at least one parameter; and
       when the thermal sensor is configured with the second set of sensor parameters, extracting the biometric data from the sensor information.

4. An apparatus supporting at least one smart application, the apparatus comprising:
   a thermal sensor interface configured to obtain sensor information from a thermal sensor and configuring the thermal sensor in accordance with a most comprehensive set of sensor parameters for all applications;
a processor for executing computer-executable instructions;
a memory storing the computer-executable instructions that when executed by the processor cause the apparatus to perform:
extracting biometric data from the sensor information;
executing the first application;
executing the second application.

5. An apparatus supporting at least one smart application with more than one thermal sensors, the apparatus comprising:
a first thermal sensor interface configured to obtain sensor information from a first thermal sensor;
a second sensor interface configured to obtain sensor information from a second thermal sensor;
a processor for executing computer-executable instructions;
a memory storing the computer-executable instructions that when executed by the processor cause the apparatus to perform:
configuring the first thermal sensor in accordance with the first set of sensor parameters;
configuring the second thermal sensor in accordance with the second set of sensor parameters;
extracting biometric data from the sensor information from all the sensors;
executing the first application:
executing the second application.

With some embodiments, the sets of configuration parameters for all the sensors may be identical, in other words, all sensors can be configured with a most comprehensive set of parameters for all applications. The best sensor configuration may include, but not limited to, highest image resolution, number of bits, frame rate, sensitivity, and signal to noise ratio (SNR).

The following is directed to vehicle operator continuous physical health monitoring embodiments.

Referring back to FIG. 1, while embodiments support assessing the health of a person in a room using a thermal sensor, embodiments may utilize thermal sensor data to assess the health of a person within other types of confined spaces such as a vehicle. The parameters used may include, but is not limited to, heart rate, breathing rate, body surface temperature, posture (in particular, head position), and the trajectories of these data over time, and so forth.

The physical health condition of a vehicle operator (vehicle driver) may be critical to the safety of the operator, the passengers, and the vehicle itself. The state of the vehicle operator condition could determine the output of a situation should an emergency arises unexpectedly.

With traditional approaches, there are numbers of ways to monitor the physical health of the vehicle operator via wearables devices. However, a wearable device is specific to the individual wearing the device and not to the vehicle and may not ensure that the information or data of the vehicle operator's health is securely monitored during the duration of the vehicle when it is in use.

With an aspect of the embodiments, monitoring of a driver and/or vehicle may be performed in an non-intrusive and accurate manner that is activated all of the time that the vehicle is in operation. Consequently, the health of whoever is driving the vehicle may be assessed. With this approach, biometric information about the driver is utilized for accident prevention, incident alert, critical health warning and postmortem analysis.

Figure 7:
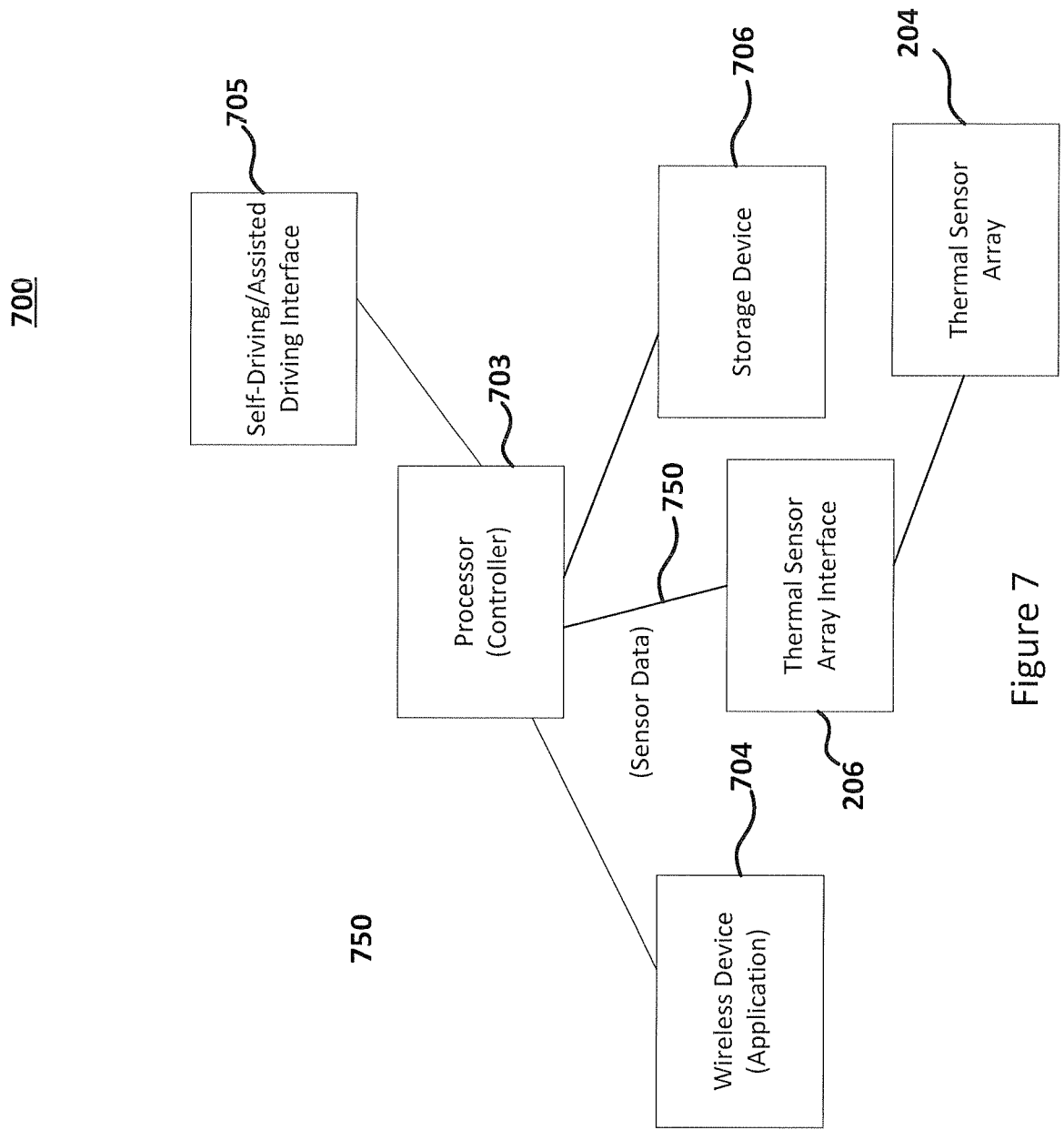
FIG. 7 shows a vehicular system for continuously monitoring a vehicular operator's physical health in accordance with an embodiment.

FIG. 7 shows vehicular system 700 for continuously monitoring a vehicular operator's physical health in accordance with an embodiment.

In reference to FIG. 2, the embodiment obtain thermal sensor data from thermal sensor 204 via thermal sensor interface 206 as previously discussed.

The thermal sensor 204 is typically fitted at a fixed location in front of the vehicle operator (driver), for example, mounted against the top windshield corner in front of the driver.

Processor 703 configures the thermal sensor by reference to methods in FIG. 5.

Processor 703 extracts biometric information contained in sensor data 750. For example, processor 703 may continuously monitor the heart rate and head posture about the driver as soon as he sits in the driving seat. In addition, the health record of the driver may be loaded into processor 703 via wireless devices 704 from a remote database server.

Processor 703 may decide addition biometric data are needed based on the health record of the driver. For example if the BMI of the driver exceeds a certain value, the change of heart rate, the change of body surface temperature, and change of head posture over time may also be monitored.

As will be discussed in further detail, processor 703 detects one or more current physical conditions about the driver and executes one or more actions to address the detected physical conditions.

Processor 703 may report detected physical conditions to the driver, doctor, emergency contact, and so forth via wireless device 704 (for example a smartphone) executing an application, initiating a telephone call to 911, generating an e-mail message to a designated person, and so forth.

Processor 703 may also initiate an action in response to the detected physical condition.

For example, if processor 703 determines that the driver is experiencing a heart attack, processor may instruct self-driving interface 704 to route the vehicle to the nearest hospital.

As will be further discussed, biometric information may be stored in storage device 706 for subsequent analysis about the health condition of the vehicle driver. While storage device 706 is shown as a separate device, storage device 706 may be integrated within wireless device 704.

Figure 8:
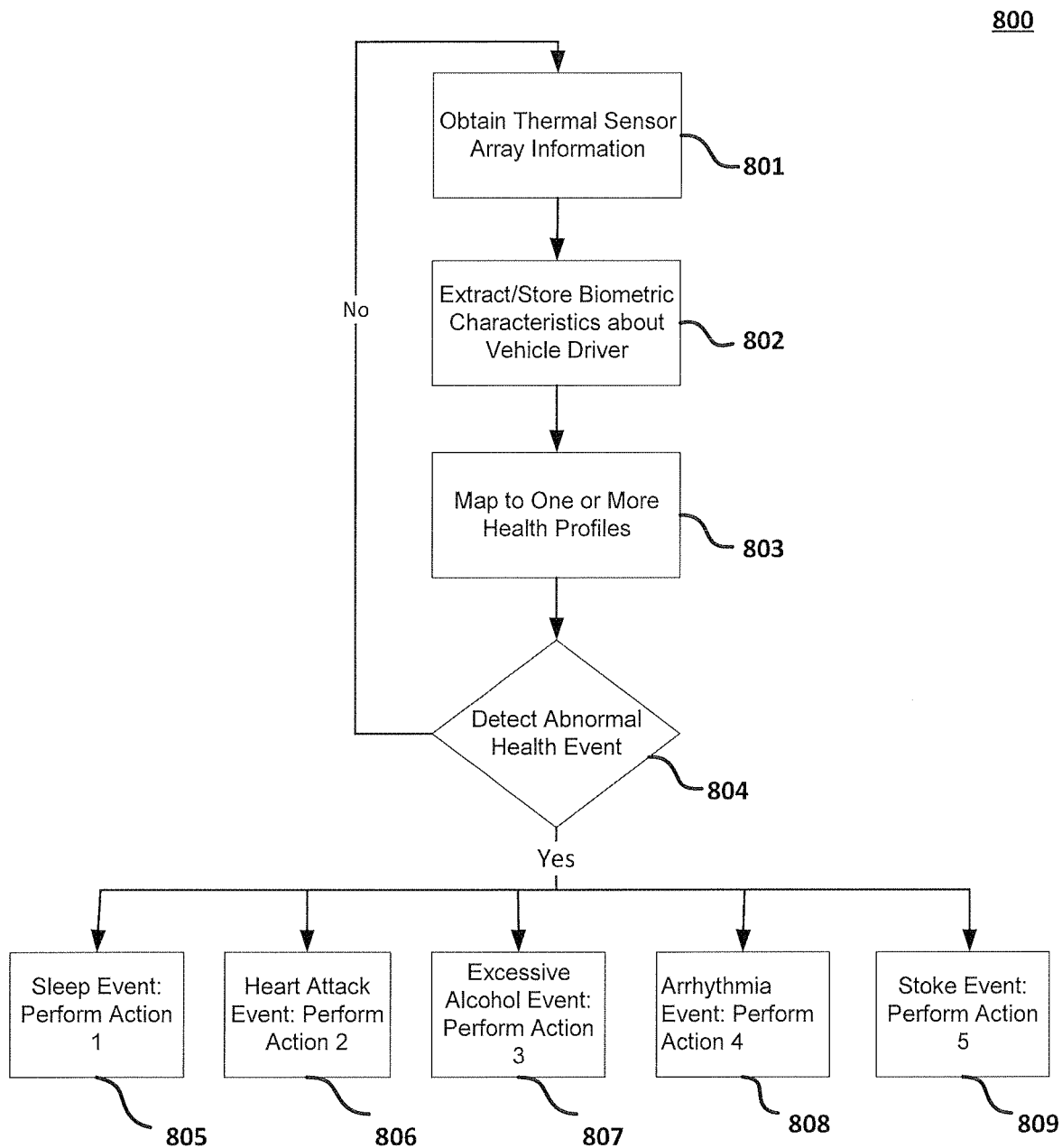
FIG. 8 shows a process that performs one or more actions based a detected physical condition of a vehicle driver in accordance with an embodiment.

FIG. 8 shows process 800 that performs one or more actions based a detected physical condition of a vehicle driver in accordance with an embodiment.

At block 801, processor 703 extracts biometric information contained in sensor data 750. Processor 703 processes the information conveyed in signal 750 to extract measurements for one or more biometric characteristics of the vehicle driver at block 802. Biometric characteristics may include, but are not limited to, heart rate, breathing rate, and deviation from average heart rate (for example, degree of heart beat irregularity).

The measurements of the biometric characteristics may be stored in storage device 706 for analysis about the health condition of the vehicle driver at a later time. For example, the stored data may be evaluated by the driver's doctor to determine if medical treatment is needed.

At block 803, process 800 obtains the measurements of the biometric characteristics (for example, the vehicle driver's heart rate and breathing rate) and determines whether a health profile applies to the drives. A plurality of health profiles may be specified, where a first health profile maps to normal vital functions of the driver (in other words, no detected health event), a second health profile maps to a heart attack event, a health third profile maps to the driver falling asleep, a fourth health profile maps to excessive alcohol consumption, and so forth.

If an abnormal health is detected based on the determined health profile is detected at block 804, process 800 detects whether a particular health event occurred at blocks 805-809. Based on a particular health event, process 800 executes an appropriate action. Exemplary actions include, but are not limited to:

Sleep event (block 805—driver falling asleep): initiate a loud warning sound through the vehicle radio or wireless device to alert the driver Heart attack event (block 806): instruct a self-driving interface to drive the vehicle to the nearest hospital Excessive alcohol consumption (block 807): prevent the vehicle driver from starting the car or safely parking the car if the car is moving Arrhythmia event (block 808—irregular heart beat or missing heart beats): generating an alert to the driver through a wireless device Stroke event (block 809): instruct a self-driving interface to drive the vehicle to the nearest hospital With an aspect of the embodiments, a processing unit continuously monitors and analyzes the heartbeat of a vehicle driver to generate an alert about any irregularity. The processing unit may use a unique algorithm to provide this capability.

With an aspect of the embodiments, a processing unit may identifying a detected irregularity to correspond to one of a plurality of events about a vehicle driver, including, but not limited to, falling asleep, a heart attack, consuming an excessive amount of alcohol, and so forth.

With an aspect of the embodiments, data about the heartbeat of a vehicle driver may be stored in a storage device. The data may be retrieved at a later time for analyzing whether an abnormal health event occurred.

As previously discussed (for example, apparatus 200 as shown in FIG. 2), biometric data is captured using thermal sensors 204 and 205. However, to enhance the robustness of a biometric system when a thermal sensor signal is blocked (for example, by furniture in smart home applications), one or more RF sensors (for example, a radar sensor) may be added to form a hybrid sensing system. While it may be difficult to identify a user only with a radar sensor, the a thermal signature of user may be obtained from a thermal sensor array and associated with a radar signal. Consequently, as will be discussed, utilizing both thermal and radar sensors may complement each other to improve the accuracy of hazard/action estimation.

Figure 9:
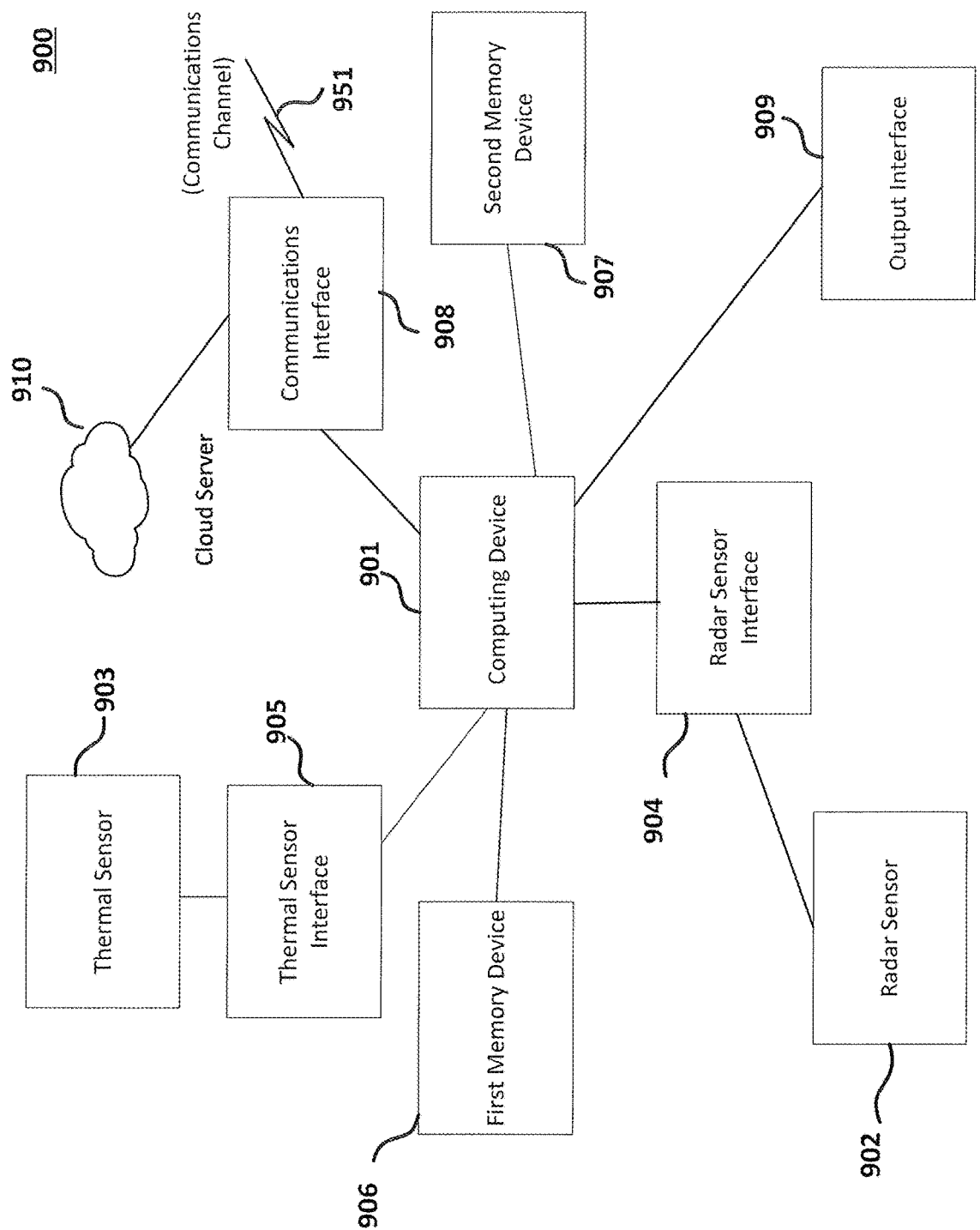
FIG. 9 shows an apparatus interfacing with a radar sensor and a thermal sensor in accordance with an embodiment.

FIG. 9 shows apparatus 900 interfacing with radar sensor 902 and thermal sensor 903 through radar sensor interface 904 and thermal sensor interface 905, respectively.

As will discussed in further detail, radar sensor 904 may comprise a transmitter transmitting a radio frequency (RF) signal in the radar spectrum (for example, operating at 20 GHz or 60 GHz) and one or more receivers detecting reflected radar signals. Apparatus 900 may subsequently extract biometric data (for example, breathing rates and motion vectors) from the detected reflected radar signals.

Thermal sensor 903 may be used for access control and presence detection. With some embodiments, in order for processor 901 to extract biometric data from thermal sensor information, the performance of thermal sensor 903 may be extended by increasing the sample frequency (for example, frame rate) of capturing the image signal, identifying and tracking individuals from the image signal, and analyzing detail changes in thermal images against time. Computing device 901 may convert sensor information (signals) to biometric data, such as heart rate, body position, health condition, and so forth.

As will be discussed in further detail, computing device 901 may utilize thermal signatures and associated motion vectors derived from thermal sensor data to assist in processing radar sensor data.

Apparatus 900 may also support prediction of future health events may by processing the sensor signals and/or support system personalization.

With some embodiments, computing device 901 may process thermal and radar sensor information to detect biometric data about a user. When a thermal signature of a particular individual is detected, computing device 901 may apply the individual's profile (for example, a temperature setting) to a smart device (for example, an air conditioner) through output interface 909.

With some embodiments, computing device 901 may support a radio frequency (RF) sensor. The RF sensor may operate in the radar spectrum (5-60 GHz).

Computing device 901 may support one or more health applications that processes and/or analyzes biometric data and may generate notifications about the biometric data to an external entity (for example, a doctor) over communications channel 951 via interface 908. As an example, a health application may detect that a user is having a possible heart attack from the biometric data; consequently, an urgent notification is sent to the user's doctor about the event. With some embodiments, if the user is driving a vehicle, the health application may stop the vehicle (though output interface 909) and report to emergency health service (though communications interface 908), and/or activate a self-driving function (via output interface 909) to drive the user to a hospital.

Apparatus 900 may also interact with cloud server 910 to enable computing device 901 to access data (for example, a health record of a user) from a remote database. For example, computing device 901 may alter a decision based on the health record of the user. In addition, apparatus 900 may continuously stream sensor data to cloud server 910 for storage or real-time analysis of the health condition of the user.

With reference to FIG. 9, a computing system environment may include a computing device where the processes (for example, processes 1003-1006 shown in FIG. 10) discussed herein may be implemented. Each process may correspond to a block of computer readable instructions that is executed by computing device 901. The computing system may include computing device 901 for controlling overall operation of the computing device and its associated components, including RAM, ROM, communications module, and first memory device 906. The computing device typically includes a variety of computer readable media. Computer readable media may be any available media that may be accessed by computing device and include both volatile and nonvolatile media, removable and non-removable media. By way of example, and not limitation, computer readable media may comprise a combination of computer storage media and communication media.

Computer storage media may include volatile and nonvolatile, removable and non-removable media implemented in any method or technology for storage of information such as computer readable instructions, data structures, program modules or other data. Computer storage media include, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by the computing device.

Communication media typically embodies computer readable instructions, data structures, program modules or other data in a modulated data signal such as a carrier wave or other transport mechanism and includes any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

With some embodiments, computing device 901 may execute computer-executable instructions stored at memory 906 and access profile data stored at memory 907.

With some embodiments, memory devices 906 and 907 may be physically implemented within a single memory device.

Figure 10:
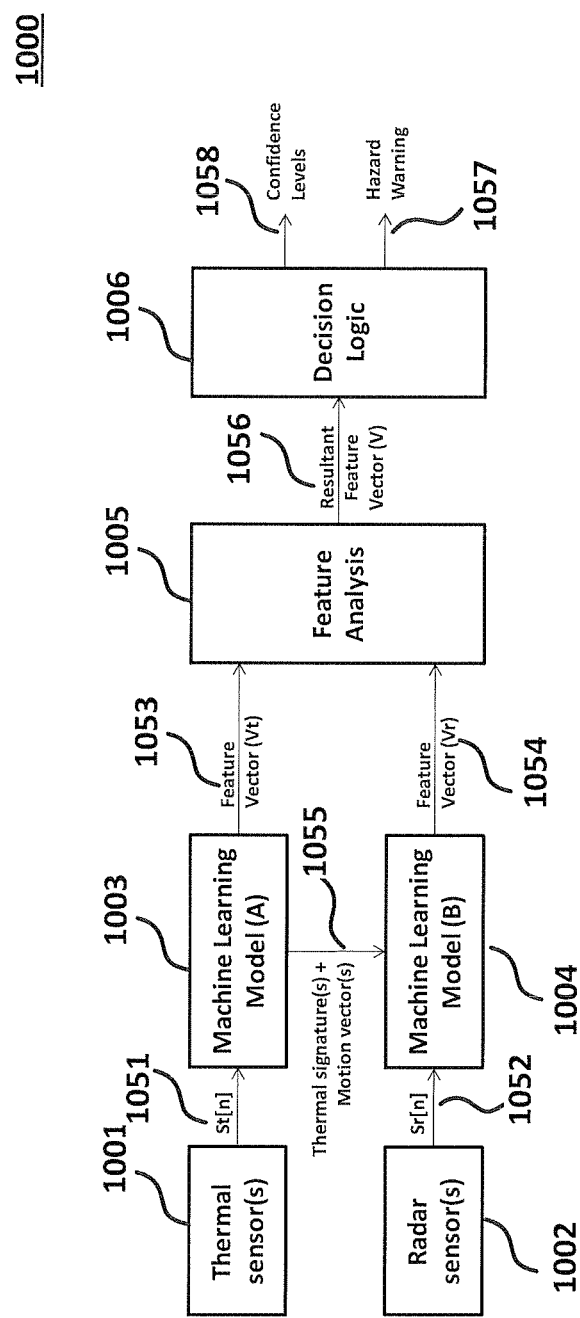
FIG. 10 shows a computing system that processes thermal and radar signals in accordance with an embodiment.

FIG. 10 shows hybrid sensing system 1000. Thermal and radar sensor data are separately captured by thermal sensor 1001 and radar sensor 1002, respectively. Depending on the complexity of the applications, thermal sensor 1001 may comprise a 32×32 thermopile array, and radar sensor 1002 may operate at 20 GHz with 1 transmit and 3 receive antennas.

The thermal and radar signals 1051 and 1052 are processed through the corresponding analytical models 1003 and 1004, respectively, to obtain biometric vectors with associated confidence levels.

Model 1003 may be a neural network model pre-trained using pre-processed thermal images and the resulting feature vectors. Model 1004 may be another neural network model pre-trained using pre-processed RF signals and the resulting feature vectors. Referring FIG. 11, model 1103 may contain models 1003 and 1004 as the first stage processing and an additional neural network layers as the second stage processing. The additional neural network layers may be trained with the feature vectors as inputs, and resultant hazard and confidence level as outputs.

As will be discussed, feature vectors 1053 and 1054 are obtained from the biometric vectors.

The biometric data extracted from thermal sensor 1001 may include, but is not limited to, breathing rates, heart rates, body surface temperatures, thermal signatures, and motion vectors. The biometric data extracted from the radar sensor 1002 may include, but is not limited to, breathing rates and motion vectors. During the sensor data acquisition phase, thermal signature(s) and the associated motion vector(s) 1055 from thermal sensor model 1003 may be provided to radar sensor model 1004 to assist its data analytic processing.

Feature vectors 1053 and 1054 are then passed to feature analytic block 1005, where vectors 1053 and 1054 are compared to obtain resultant feature vector 1056. Resultant feature vector 1056 is then passed to decision logic block 1006 for risk analysis to provide hazard level 1057 and corresponding confidence level 1058.

The following discusses a hypothetical example for apparatus 1000, where biometric data vectors $V_r$ and $V_t$ convey one or more features. Moreover, $V_t$ may convey additional features that are not conveyed by $V_r$.

Biometric data vector $V_r$ from radar sensor model 1004 may be $V_r=[B_{rb}, C_{rb}, B_{rx}, B_{ry}, C_{rm}]$, where $B_{rb}$ is the measured breathing rate and $C_{rb}$ is the confidence level of the measured breathing rate ranging from 0.0 to 1.0 in an increasing level of confidence. $B_{rx}$ and $B_{ry}$ are the components of the motion vector in X and Y, respectively, with the confidence level $C_{rm}$. A confidence level of 0 is indicative that the measurement is inconclusive.

Concurrently, biometric data vector $V_t$ from thermal sensor 1001 may be $V_t=[B_{rb}, C_{rb}, B_{tx}, B_{ty}, C_{tv}]$, where $B_{rb}$ and $C_{th}$ are the measured breathing rate and associated confidence level and $B_{tx}$, $B_{ty}$, and $C_{tm}$ are the motion vector in X and Y with associated confidence level $C_{tm}$.

Biometric vectors $V_r$ and $V_t$ include a measured value and corresponding confidence level for one or more biometric features. For example, with the examples shown above, $V_r$ and $V_t$ span breathing rate and motion features.

Feature vectors 1053 and 1054 are then processed by feature analysis block 1005.

Figure 12:
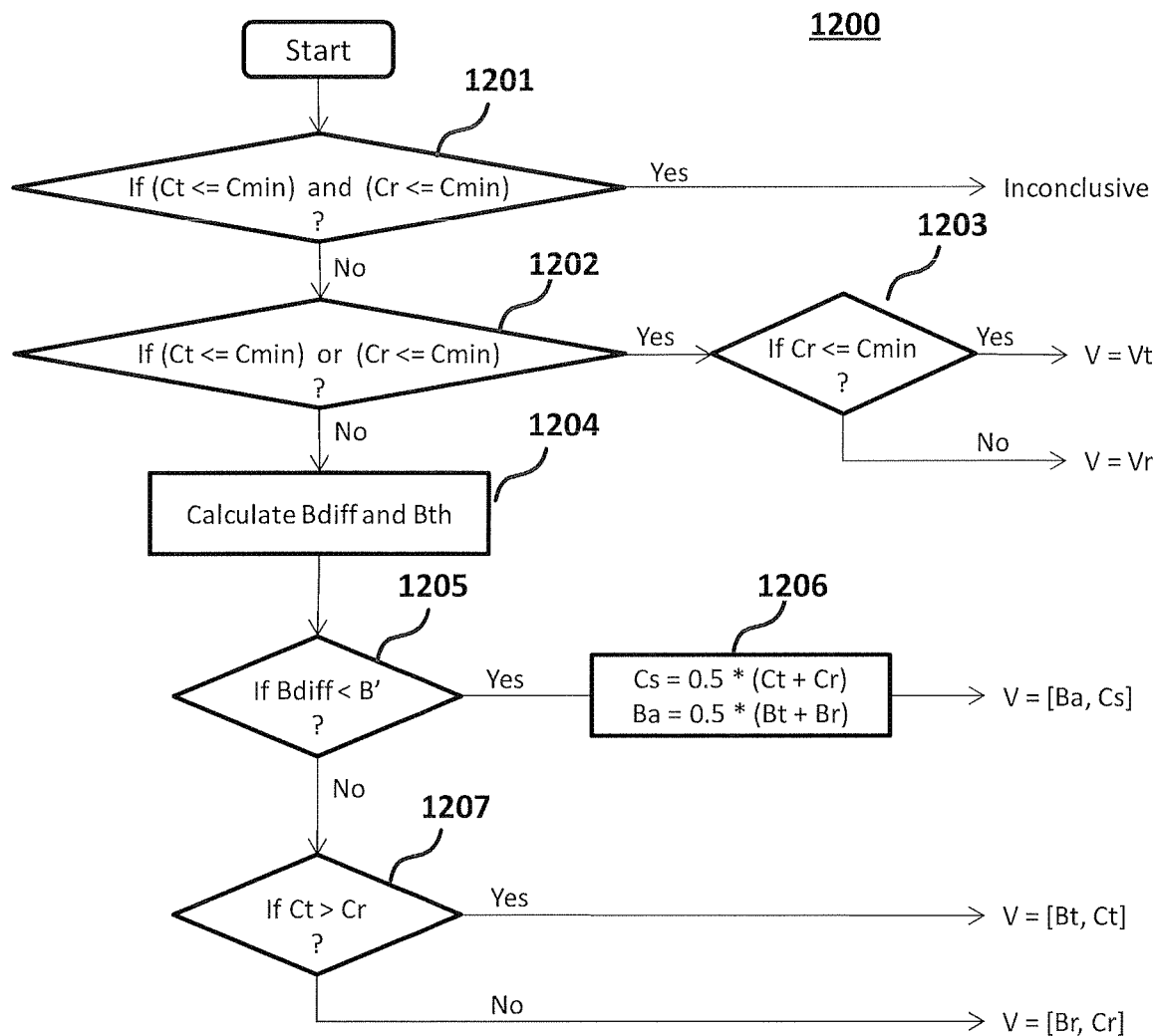
FIG. 12 shows a flow chart for performing feature analysis in accordance with an embodiment.

Exemplary flow chart 1200 for feature analysis logic block 1005 is shown in FIG. 12. A biometric feature (for example, the breathing rate) of the same type may pass through a decision matrix to obtain resultant feature vector V 1056.

For example, when biometric vectors at time t1 are $V_{r1}=[25, 0.90, 0, 0, 0.80]$ and $V_{t1}=[23, 0.80, 0, 0, 0.90]$, breathing rate vectors 1053 and 1054 are equal to [25,0.9] and [23,0.8], respectively.

Referring to flow chart 1200 shown in FIG. 12, process 1200 determines a resultant feature vector (V) 1056, where V=[B,C], B is the measured feature value, and C is the corresponding confidence level. For example, the biometric feature may be the breathing rate.

Feature vector 1053 $V_t=[B_t, C_t]$ and feature vector 1054 $V_r=[B_r, C_r]$. With flow chart 1200, $C_{min}=0.6$. $C_{min}$ is the minimum confidence level for a measured value to be considered. The confidence level may be chosen based on empirical results. It may also be adaptive based on the quality of the sensor signals.

At step 1201, if both $C_t$ and $C_r$ are less than $C_{min}=0.6$, the results are inconclusive.

Otherwise, at step 1202 process 1200 will discard the feature vector having a confidence level less than $C_{min}=0.6$. In other words at step 1203, if $C_r<0.6$, $V=V_t$. Otherwise, $V=V_r$.

At step 1204, process 1200 determines $B_{diff}$ and $B_{th}$, where $B_{diff}=|B_t-B_r|$ and $B_{th}=0.1*(0.5*(B_t+B_r))$.

If $B_{diff}<B_{th}$, as determined at step 1205, then $V=[B_a,C_s]$ at step 1206 where $B_a=0.5*(B_t+B_r)$ and $C_s=0.5*(C_t+C_r)$.

Otherwise if Bdiff>=Bth, if Ct>Cr, as determined at step 1207, V=[Bt,Ct]. Otherwise, V=[Br,Cr].

As an example, let biometric vector $V_t=[25.0.9]$ and $V_r=[23,0.8]$. Processing $V_t$ and $V_r$ through feature analysis logic block 1005 in accordance with process 1200, one determines the resultant feature vector [24,0.85], corresponding to a breathing rate of 24 and a confidence level of 0.85.

If biometric vectors span more than one feature (for example, breathing rate and motion), each feature may be separately processed by process 1200. For example, by processing biometric vectors $V_{r1}=[25, 0.90, 0, 0, 0.80]$ and $V_{t1}=[23, 0.80, 0, 0, 0.90]$, the resultant biometric vector feature V would be: $V_1=[24, 0.85, 0, 0, 0.85]$.

When only one biometric vector $V_r$ or $V_t$ contains feature information $(B_i,C_i)$ for the $i^{th}$ feature (for example, heart rate), feature analysis logic block 1005 may use feature information ($B_i, C_i$) when $C_i >= C_{min}$ for constructing the resultant biometric vector.

Referring back to FIG. 10, decision logic block 1006 determines hazard level 1057 and its associated confidence level 1058. For the above example of $V_1$, since the breathing rate is normal the potential hazard is low with a confidence level, for example, 0.7 (high) although there is no detected movement for the identified subject (user). However, the value of the confidence level may be adjusted based on empirical results associated with an embodiment. Decision logic block 1006 continuously monitors resultant feature vector 1056, as well as its evolvement over time, to determine a potential hazard measure (corresponding hazard warning 1057). For example, the resultant biometric vectors of the eight consecutive measurements may be: $V_1$=[24, 0.85, 0, 0, 0.85], $V_2$=[23, 0.87, 0, 0, 0.88], $V_3$=[21, 0.89, 0, 0, 0.82], $V_4$=[18, 0.85, 0, 0, 0.85], $V_5$=[14, 0.87, 0, 0, 0.90], $V_6$=[9, 0.86, 0, 0, 0.95], $V_7$=[5, 0.83, 0, 0, 0.90], and $V_8$=[0, 0.85, 0, 0, 0.90].

Decision logic block 1006 may determine that the hazard level is high and the confidence level (0.6) is medium at the $5^{th}$ measurement because the breathing rate of the subject is dropping and there is no movement detection. However, decision logic block 1006 may determine that the hazard level is high and confidence level (0.8) is high at the $7^{th}$ measurement because the breathing level of the subject is dropping rapidly to a hazardous level and there was no movement detected over seven consecutive measurements.

The detection accuracy may be improved if more biometric data (corresponding to additional features) are obtained from sensors 1001 and/or 1002. For instance, heart rate and thermal signature may also be obtained from thermal sensor 1001. For example, $V_t$=[$B_{tb}$, $C_{tb}$, $B_{th}$, $C_{th}$, $B_{tt}$, $C_{tt}$, $B_{ts1}$, $C_{ts1}$, $B_{tx}$, $B_{ty}$, $C_{tv}$], where $B_{tb}$, $C_{tb}$ corresponds to the measured breathing rate, $B_{th}$, $C_{th}$ corresponds to the measured heart rate, $B_{tt}$, $C_{tt}$ corresponds to the measured body surface temperature, $B_{ts1}$, $C_{ts1}$ corresponds to the thermal signature of an associated entity (for example, registered user1), and $B_{tx}$, $B_{ty}$ and $C_{tm}$ corresponds to the motion vector in X and Y with the confidence level $C_{tm}$.

Referring to the previous example, assume that biometric vectors are $V_{r1}$=[25, 0.90, 0, 0, 0.80] and $V_{tt}$=[23, 0.80, 80, 0.85, 37.0, 0.90, 1, 0.90, 0, 0, 0.90]. The resultant biometric vector (as determined by feature analysis block 1005 in accordance with process 1200) is $V_1$=[24, 0.85, 80, 0.85, 37.0, 0.90, 1, 0.90, 0, 0, 0.85]. From decision logic block 1006, the hazard level would be low with confidence level 0.8 (high) as all biometric data of the identified subject (user1) are normal.

As example, the time sequence of the resultant biometric vectors may be $V_1$=[24, 0.85, 80, 0.85, 37.0, 0.90, 1, 0.90, 0, 0, 0.85], $V_2$=[23, 0.87, 77, 0.90, 37.1, 0.90, 1, 0.90, 0, 0, 0.88], $V_3$=[21, 0.89, 72, 0.87, 37.0, 0.87, 1, 0.90, 0, 0, 0.82], $V_4$=[18, 0.85, 66, 0.85, 37.0, 0.90, 1, 0.90, 0, 0, 0.85], $V_5$=[14, 0.87, 60, 0.86, 36.9, 0.89, 1, 0.90, 0, 0, 0.90], $V_6$=[9, 0.86, 55, 0.88, 36.9, 0.90, 1, 0.90, 0, 0, 0.95], $V_7$=[5, 0.83, 50, 0.86, 36.7, 0.90, 1, 0.90, 0, 0, 0.90], and $V_8$=[0, 0.85, 45, 0.87, 36.7, 0.90, 1, 0.90, 0, 0, 0.90].

With the above time sequence, decision logic block 1006 may estimate a hazard level as being high with confidence level 0.8 (high) for the identified subject (user1) after the $5^{th}$ measurement since both the breathing rate and heart rate are dropping together. Moreover, because user1 is detected via thermal signature, more valuable information may be provided, such as reporting the hazard level and confidence level to the registered hospital of user1 and preparing the medical care of user1 before arrival to the hospital.

While not explicitly shown in FIG. 10, with some embodiments, hazard prediction may also be done solely by using solely machine learning models 1003 and 1004.

Figure 11:
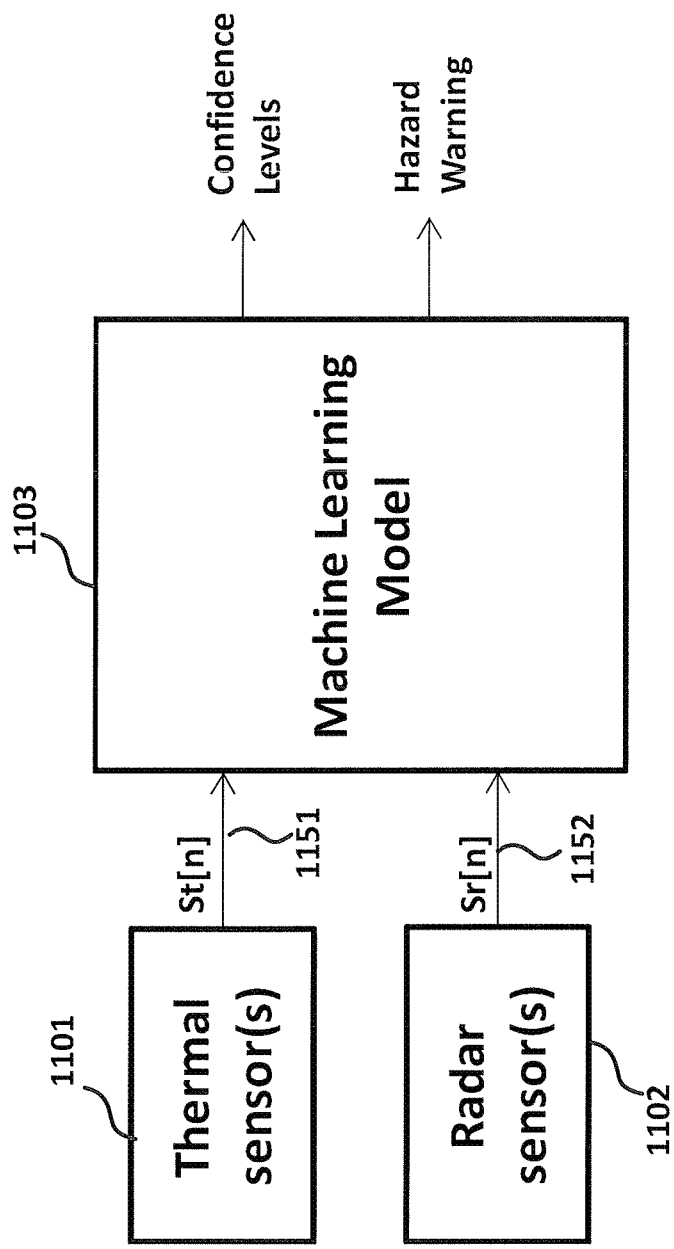
FIG. 11 shows a computing system that processes thermal and radar signals in accordance with an embodiment.

An alternative approach, with the embodiment shown in FIG. 11, outputs 1151 and 1152 from both sensors 1101 and 1102 are directly fed into analytical model 1103. Analytical model 1103 may be an artificial neural network pre-trained with artificial vectors extracted from clinical data. Analytical model 1103 may be fine-tuned (re-trained) with empirical data directly obtained from the field.

With some embodiments, combinations of thermal sensors and radar sensors may be installed through an associated entity (for example, a house or business) to ensure a desired coverage with optimal system cost in smart home/business applications. For example, a thermal sensor and a radar sensor may be installed in the sitting room as well as in each bed room. However, only thermal sensor arrays may be installed near a toilet and in the kitchen and/or the garage.

Figure 13:
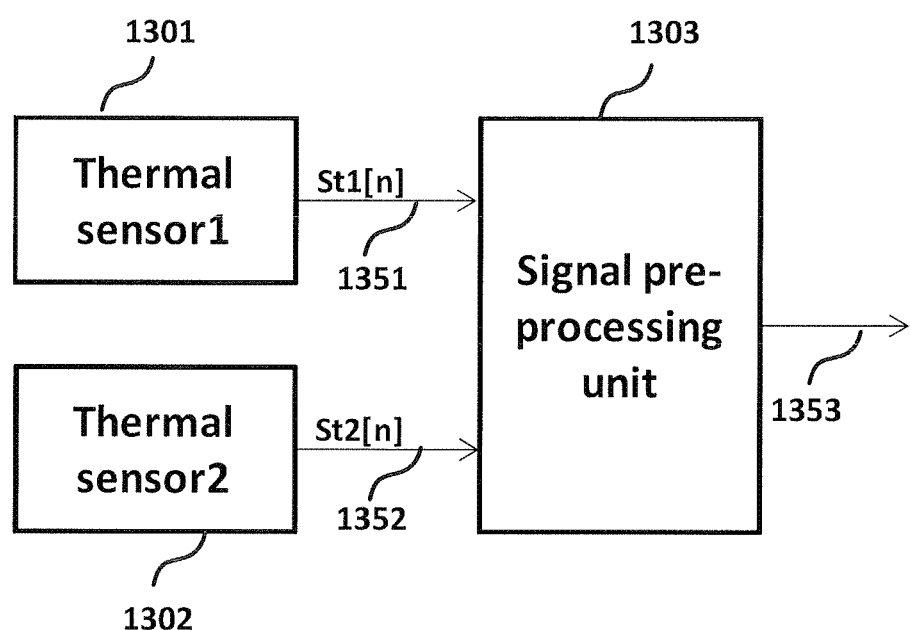
FIG. 13 shows pre-processing of thermal signals in accordance with an embodiment.

With another smart home application, there may be two thermal sensors plus a radar sensor installed in the sitting room. Signals 1351 and 1352 from two thermal sensors 1301 and 1302 may be pre-processed by signal pre-processing unit 1303, as shown in FIG. 13, to obtain a resultant thermal sensor signal 1353, which may be provided to the systems shown in FIG. 10 or FIG. 11. With some embodiments, signal pre-processing may include high-pass filtering the image signals over time and choosing the one with the higher residual. With some embodiments, signal pre-processing unit 1303 may include stitching the two thermal sensor signals 1351 and 1352 to form a better thermal sensor signal. Alternatively, machine learning models 1003 and 1004 (as shown in FIG. 10) or machine learning model 1103 (as shown in FIG. 11) may be re-trained for a specific combination of thermal sensors and radar sensors without signal pre-processing.

With some embodiment, a hybrid sensing system may be inside vehicle to increase the accuracy in monitoring the physical health condition of a vehicle operator (vehicle driver) to reduce the chance of false detections. The state of the vehicle operator condition may determine a course of action should an emergency happen.

Figure 14:
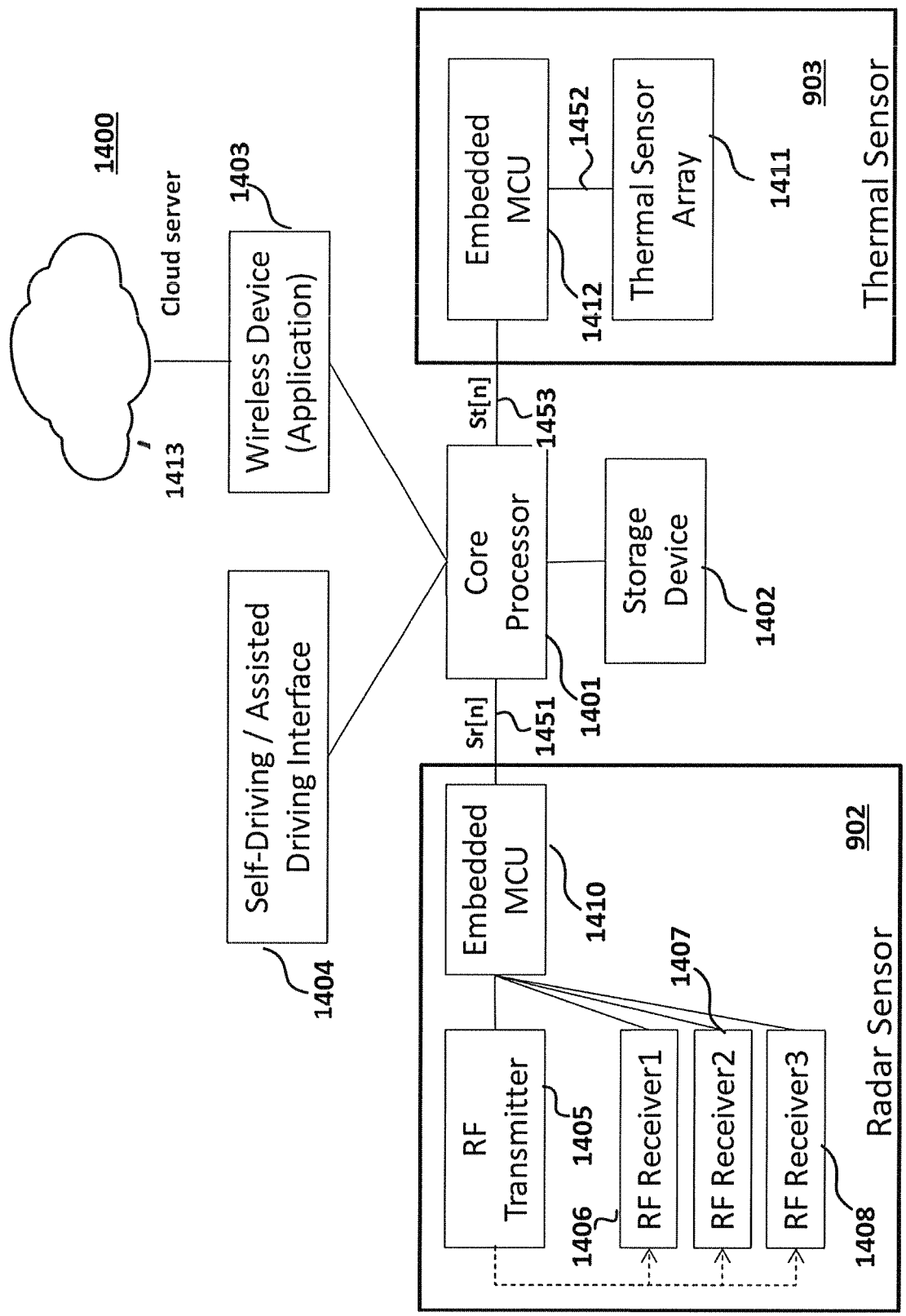
FIG. 14 shows a sensing system for a vehicle in accordance with an embodiment.

Referring to FIG. 14, hybrid sensing system 1400 continuously monitors a vehicular operator's physical health for a vehicle application as shown. Hybrid sensing system 1400 includes radar sensor 902 and thermal sensor 903.

Radar sensor 902 includes RF transmitter 1405, which is typically fitted at a fixed location in front of the vehicle operator (driver) (for example, mounted against the top windshield corner in front of the driver such that the signal from the transmitter is reflected by the driver's body to the receiver without obstructed by any uninterested moving objects, such as the steering wheel). RF transmitter 1405 generates fixed frequency signal, for example, between 20-30 GHz with a power level between 0.1-0.5 watts depending on the RF characteristics of the vehicle.

RF signals received by receivers 1406-1408 are processed by embedded microcontroller unit (MCU) 1410 to obtain radar signal 1451, which is suitable for a corresponding machine learning model.

Thermal sensor 903 is typically physically situated next to radar sensor 902 to capture thermal signal 1452 via thermal sensor array 1411 from the driver's head as well as the body. Thermal signal 1452 is processed by embedded MCU 1412 to output signal 1453, which is suitable for a corresponding machine learning model.

Core processor 1401 executes computer readable instructions stored at device 1402 to support machine learning models for thermal sensor 903 and radar sensor 902, feature analysis block 1005, and decision logic block 1006 as shown in FIG. 10. With some embodiments, core processor 1401 may have a machine learning model implemented for both sensor types as shown in FIG. 11.

When core processor 1401 detects any hazardous physical conditions about the driver, it may execute one or more actions to address the detected physical conditions. The list of actions includes, but not limited to, reporting the detected physical conditions to the driver, doctor, or emergency contact via embedded wireless device 1403 (for example, an LTE module) installed in the hybrid sensing system 1400, initiating a telephone call to 911, and generating an e-mail message to a designated person.

Wireless device 1403 may allow the health record of the driver to be loaded into core processor 1401 via the wireless devices from a remote database server. The parametric of the decision logic supported by core processor 1401 may be altered based on the heath record of the driver.

In addition, wireless device 1403 may also allow the sensor data to be continuously streamed to cloud server 1413 for storage or for real-time analyzing the health condition of the driver (if one chooses to execute the analytic model in the cloud instead of locally or to execute the model both locally as well as in the cloud for cross-checking purposes). Cloud server 1413 may use the data from hybrid sensor system 1400 to fine-tune the analytic model. Moreover, system 1400 may train new models based on new sensor combinations. The re-trained or new analytic models may be downloaded from cloud server 1413 to the core processor 1401 to continuously improve the accuracy of the analytic models.

Downloaded information from cloud server 1413 may include a chronicle health record and the conduct record of the user (driver) for reference. For example, if the downloaded conduct record indicates that the user has previously driven while intoxicated, system 1400 may extract pertinent feature information that may be indicative of intoxication so that appropriate actions can the performed.

Also, system 1400 may send the record of the driver's conduct to a control center if system 1400 detects a hazard in order to assist with a decision making process. The chronicle health record, as well as the driver's conduct record, may be sent to an emergency service when a hazard occurs to allow for better preparation when the user arrives at the hospital.

All the downloaded information (for example, the sensor data as well as system outputs) may be temporarily stored in storage device 1402 (which may also store computer readable instructions as previously discussed). The data may be retained until it is cleared by authorized persons, for example, after the data is backed up at the end of business hours. Moreover, the data may be retrieved under certain conditions by authorized persons, for example, when an accident happens that involves the user.

Core processor 1401 may store biometric data (for example, sensor data, biometric vectors, and/or resultant biometric vectors) at storage device 1402. The stored biometric data may be subsequently retrieved to reconstruct an health event that occurred or to provide data for legal evidence.

Advanced functions may be implemented by core processor 1401 when computational power is available. For example, if core processor 1401 determines that the user (driver) is experiencing a heart attack, it may instruct initiate an autonomous driving unit via interface 1404 to route the vehicle to the nearest hospital.

As previously discussed, a thermal signal (for example, from thermal sensor 903) may be blocked (and consequently not available) in some situations; however, a received RF signal (for example, from radar sensor 902) may be processed by itself to assess the vehicular operator's physical health.

Figure 15:
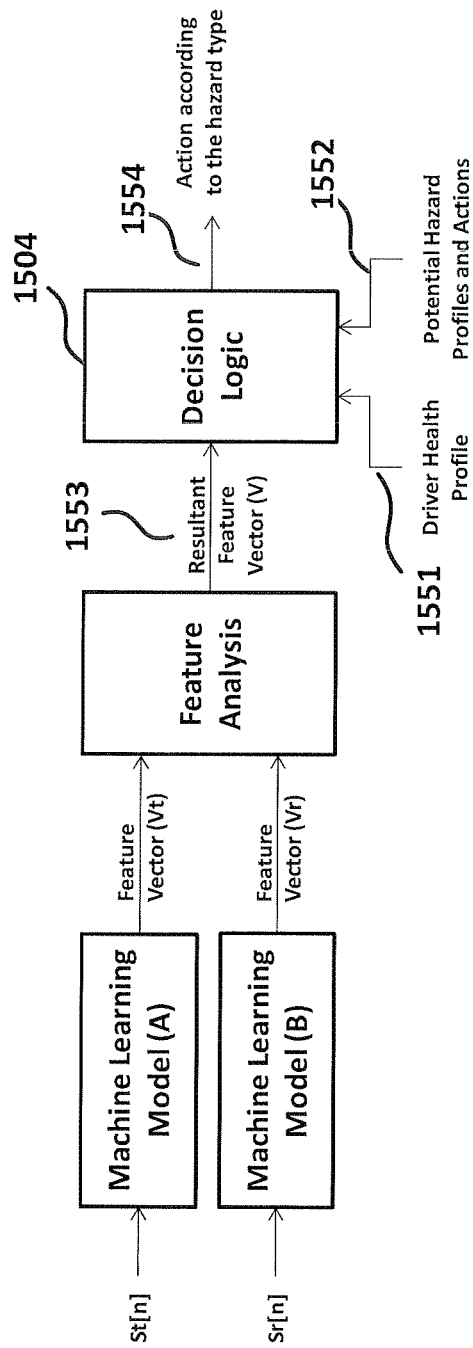
FIG. 15 shows a computing system that processes biometric signals in a vehicle in accordance with an embodiment.

FIG. 15 shows an embodiment of the processing that may supported by system 1400. The sequence of actions is similar to the ones as discussed with FIG. 10. Health record 1551 of the driver and profiles of the hazards to be detected/the associated actions for each hazard 1552 may loaded into decision logic block 1504. By presenting feature vector to decision logic, block 1504 is able to detect a particular hazard and to perform associated actions 1554 from presented feature vectors 1553.

Figure 16:
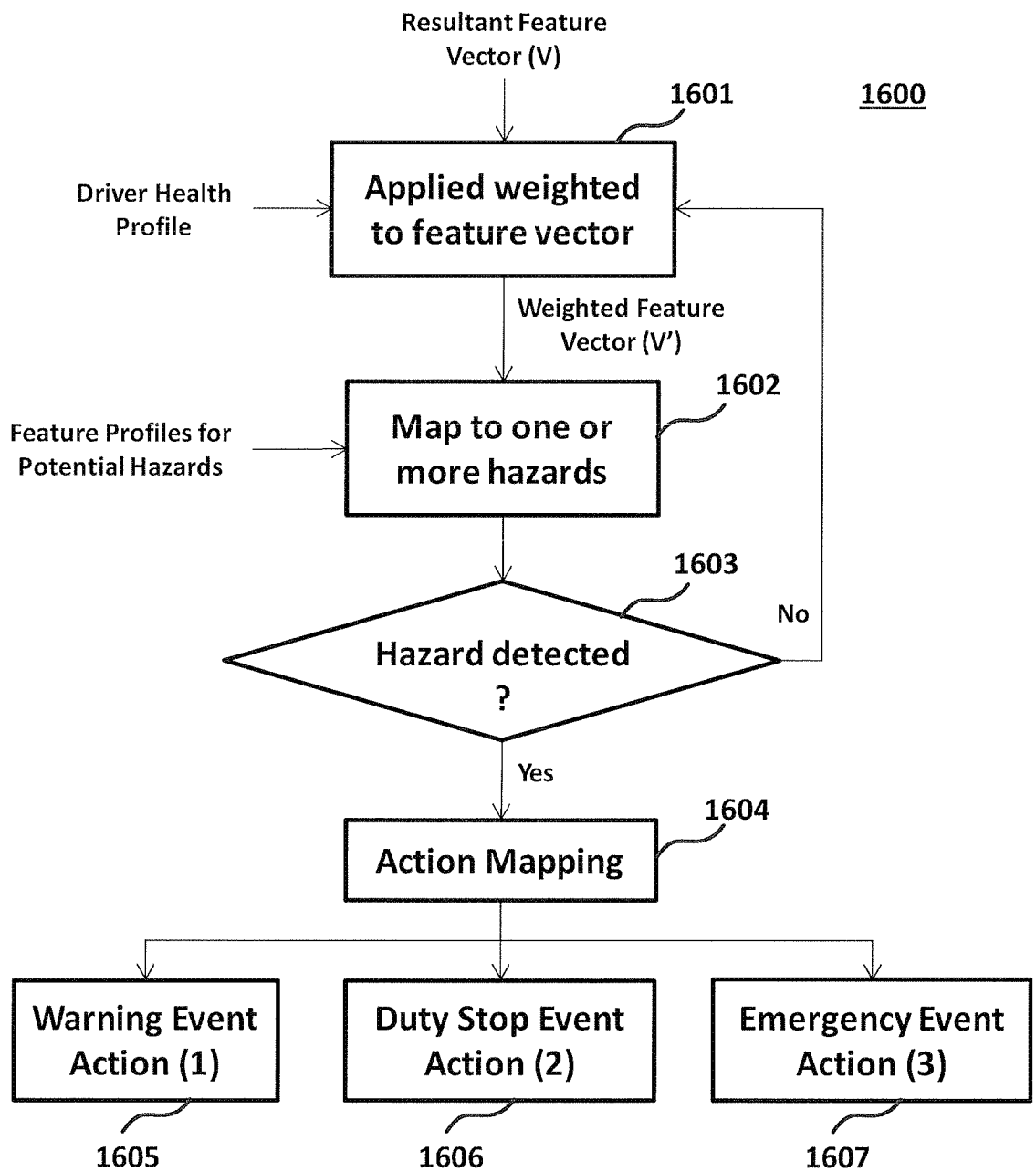
FIG. 16 shows a flow chart for a decision logic block in accordance with an embodiment.

FIG. 16 shows flow chart 1600 for decision logic block 1504. Different weightings may be applied to the elements (for example, corresponding to different feature information) in the resultant feature vector based on the health record of the driver. For example, if the driver is over certain age (for example, 55 years of age) and is obese (for example, 85 kg and 1.68 m), more weight can be applied to the change of heart rate over time and to the breathing rhythm. As another example, if the user (driver) has a record of being a careless driver, more weight can be applied to the motion vectors. The weighted feature vector is then mapped to the list of hazards. An exemplary list of hazards may be:

| Hazard type | Action type | Actions |
| --- | --- | --- |
| Sleep | Warning event | Activate the alert in the vehicle |
| Unconscious | Emergency event | Stop vehicle and report to emergency health service, or Switch to self-driving function to the emergency health service |
| Abnormal driving pattern | Duty stop event | Stop vehicle and request for backup driver |
| Abnormal heart rate pattern | Duty stop event | |
| Abnormal breathing pattern | Duty stop event | |
| Abnormal body surface temperature change pattern | Duty stop event | |

When a match of the hazard type is found, the list of associated actions may be performed. For example, if the driver is determined to be tired and prone to driving while asleep, the alert system in the vehicle may be activated in order to wake the driver. As another example, if critical biometric data is found to be abnormal (for example, a change of heart rate is abnormal), the alert system may instruct the driver to pull over the vehicle and a message may be sent to the control center to request a backup driver to take over the driving. As another example, if the driver is detected to be unconscious, the alert system in the vehicle may stop the vehicle. Moreover, the alert system may automatically request for emergency health service. If autonomous driving is available with the vehicle, the vehicle may be self-driven to the nearest emergency health service.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

What is claimed is:

1. An apparatus supporting biometric data about a user, the apparatus comprising:
a thermal sensor interface configured to obtain a thermal signal from a thermal sensor;
a radar sensor (RF) interface configured to obtain a radar signal from a radar sensor;
a processor for executing computer-executable instructions;
a memory storing the computer-executable instructions that when executed by the processor cause the apparatus to perform:
generating a first biometric vector from the thermal signal, wherein the first biometric vector contains first information about a first biometric feature and wherein the first biometric vector contains third information about a second biometric feature;
generating a second biometric vector from the radar signal, wherein the second biometric vector contains second information about the first biometric feature and wherein the second biometric vector contains fourth information about the second biometric feature;
extracting first resultant information about the first biometric feature from the first and second information;
generating a first resultant biometric vector containing the first resultant information about the first biometric feature;
generating the first resultant biometric vector containing second resultant information about the second biometric feature;
based on a health record of the user, applying a first weight to the first resultant information about the first biometric feature and a second weight to the second resultant information about the second biometric feature, wherein the first weight and the second weight are different; and
determining hazard information from the first resultant biometric vector, wherein the hazard information includes a hazard level and a confidence level and wherein the hazard level is indicative of an occurrence of a health event for the user and the confidence level is indicative of a degree of certainty of the hazard level.

2. The apparatus of claim 1, wherein the memory storing computer-executable instructions that when executed by the processor further cause the apparatus to perform:
when the thermal signal is not available, extracting the first resultant information about the first biometric feature only from the second information contained the second biometric vector from the radar signal.

3. The apparatus of claim 1 comprising:
a communications interface,
wherein the memory storing computer-executable instructions that when executed by the processor further cause the apparatus to perform:
extracting a thermal signature from the thermal signal, wherein the thermal signature identifies the user; and
when the health event is detected, sending a message indicative of the hazard level about the user through the communications interface.

4. The apparatus of claim 3, wherein the hazard information includes a hazard type and wherein the memory storing computer-executable instructions that when executed by the processor further cause the apparatus to perform:
downloading and storing the health record of the user;
including at least a portion of the health record in the message;
identifying an action mapped to the hazard type; and
executing the identified action on behalf of the user.

5. The apparatus of claim 1, wherein the memory storing computer-executable instructions that when executed by the processor further cause the apparatus to perform:
determining a hazard type from the first resultant biometric vector;
identifying an action mapped to the hazard type; and
performing the identified action on behalf of the user.

6. The apparatus of claim 5, wherein the hazard type is one of a plurality of hazard types and wherein the memory storing computer-executable instructions that when executed by the processor further cause the apparatus to perform:
grouping the plurality of hazard types with different importance levels; and
generating an alert warning based on the different importance levels.

7. The apparatus of claim 5, wherein the memory storing computer-executable instructions that when executed by the processor further cause the apparatus to perform:
generating a time sequence of resultant biometric vectors, wherein the time sequence comprises the first resultant biometric vector and a second resultant biometric vector corresponding to first and second time instances, respectively; and
determining the hazard level from the time sequence of resultant biometric vectors.

8. The apparatus of claim 1, wherein the memory storing computer-executable instructions that when executed by the processor further cause the apparatus to perform:
training a first model based on a previously occurring thermal signal;
transforming the thermal signal in accordance with the first model;
obtaining the first biometric vector from the transformed thermal signal;
training a second model based on a previously occurring radar signal;
providing a thermal signature and a motion vector from the first model to the second model;
transforming the radar signal in accordance with the second model, the thermal signature, and the motion vector; and
obtaining the second biometric vector from the transformed radar signal.

9. The apparatus of claim 8, wherein the first model comprises a first neural network model, wherein the second model comprises a second neural network model, and wherein the memory storing computer-executable instructions that when executed by the processor further cause the apparatus to perform:
pre-training the first neural network model using a pre-processed image and a first resulting feature vector; and
pre-training the second neural network model using a pre-processed RF signal and a second resulting feature vector.

10. The apparatus of claim 9, wherein a combined neural network model comprises a first neural stage and a second neural stage and wherein the memory storing computer-executable instructions that when executed by the processor further cause the apparatus to perform:

applying the first neural network model and the second neural network model to the first neural stage; and
training the second neural stage with the resulting feature vectors as inputs and a resultant hazard and a confidence level as outputs.

11. The apparatus of claim 8, wherein the memory storing computer-executable instructions that when executed by the processor further cause the apparatus to perform:
downloading the first and second models from a cloud server;
receiving updated model information from the cloud server; and
updating at least one of the first and second models based on updated model information.

12. The apparatus of claim 11, wherein the memory storing computer-executable instructions that when executed by the processor further cause the apparatus to perform:
sending, to the cloud server, biometric information about the first and second biometric vectors.

13. A method for assessing a health condition of a user, the method comprising:
obtaining thermal signal from a thermal sensor;
obtaining a radar signal from a radar sensor;
generating a first biometric vector from the thermal signal, wherein the first biometric vector contains first information about a first biometric feature and wherein the first biometric vector contains third information about a second biometric feature;
generating a second biometric vector from the radar signal, wherein the second biometric vector contains second information about the first biometric feature and wherein the second biometric vector contains fourth information about the second biometric feature;
extracting first resultant information about the first biometric feature from the first and second information;
generating a first resultant biometric vector containing the first resultant information about the first biometric feature; and
generating the first resultant biometric vector containing second resultant information about the second biometric feature;
based on a health record of the user, applying a first weight to the first resultant information about the first biometric feature and a second weight to the second resultant information about the second biometric feature, wherein the first weight and the second weight are different; and
determining hazard information from the first resultant biometric vector, wherein the hazard information includes a hazard level and a confidence level and wherein the hazard level is indicative of an occurrence of a health event for the user and the confidence level is indicative of a degree of certainty of the hazard level.

14. The method of claim 13 comprising:
when the thermal signal is not available, extracting the first resultant information about the first biometric feature only from the second information contained the second biometric vector from the radar signal.

15. The method of claim 13 comprising:
extracting a thermal signature from the thermal signal, wherein the thermal signature identifies the user; and
when the health event is detected, sending a message indicative of the hazard level about the user.

16. The method of claim 15, wherein the hazard information includes a hazard type, the method comprising:
downloading and storing the health record of the user;
including at least a portion of the health record in the message;
identifying an action mapped to the hazard type; and
executing the identified action on behalf of the user.

17. The method of claim 13 comprising:
sending the first and second biometric vectors to a cloud server; and
receiving the hazard information from the cloud server.

18. The method of claim 13 comprising:
determining a hazard type from the first resultant biometric vector;
identifying an action mapped to the hazard type; and
performing the identified action on behalf of the user.

19. The method of claim 13, wherein the first biometric vector contains fifth information about a third biometric feature and the second biometric vector does not contain any information about the third biometric feature, the method comprising:
extracting second resultant information about the third biometric feature only from the fifth information.

20. An apparatus providing an assessment of a vehicle driver of a vehicle, the apparatus comprising:
a thermal sensor interface configured to obtain a thermal signal from a thermal sensor;
a radar sensor (RF) interface configured to obtain, from a radar sensor, a radar signal reflected by the vehicle driver;
a processor for executing computer-executable instructions;
a memory storing the computer-executable instructions that when executed by the processor cause the apparatus to perform:
generating a first biometric vector from the thermal signal, wherein the first biometric vector contains first information about a first biometric feature;
generating a second biometric vector from the radar signal, wherein the second biometric vector contains second information about the first biometric feature;
extracting first resultant information about the first biometric feature from the first and second information;
generating a first resultant biometric vector containing the first resultant information about the first biometric feature;
determining a hazard type from the first resultant biometric vector, wherein the hazard type is indicative of an occurrence of a health event for the vehicle driver;
identifying an action mapped to the hazard type;
performing the identified action on behalf of the vehicle driver;
downloading a chronicle health record and conduct record of the vehicle driver; and
identifying the identified action based on the chronicle health and conduct record.

21. The apparatus of claim 20, wherein the identified action is indicative of switching to a self-driving function, the apparatus comprising:
a self-driving interface, wherein the memory storing computer-executable instructions that when executed by the processor further cause the apparatus to perform:
instructing, through the self-driving interface, the vehicle to be self-driven to an emergency health service.

22. The apparatus of claim 20, wherein the memory storing computer-executable instructions that when executed by the processor further cause the apparatus to perform:

based on the chronicle health and conduct record of the vehicle driver, applying a first weight to the first resultant information about the first biometric feature and a second weight to a second resultant information about a second biometric feature, wherein the first weight and the second weight are different.

23. The apparatus of claim 20, wherein the memory storing computer-executable instructions that when executed by the processor further cause the apparatus to perform:

when the health event is detected, sending the chronicle health and conduct record to an emergency service.

24. An apparatus providing an assessment of a vehicle driver of a vehicle, the apparatus comprising:

a radar sensor (RF) interface configured to obtain, from a radar sensor, a radar signal reflected by the vehicle driver;

a processor for executing computer-executable instructions;

a memory storing the computer-executable instructions that when executed by the processor cause the apparatus to perform:

generating a biometric vector from the radar signal, wherein the biometric vector contains information about a first biometric feature;

extracting first resultant information about the first biometric feature from the information;

generating a first resultant biometric vector containing the first resultant information about the first biometric feature;

determining a hazard type from the first resultant biometric vector, wherein the hazard type is indicative of an occurrence of a health event for the vehicle driver;

identifying an action mapped to the hazard type;

performing the identified action on behalf of the vehicle driver;

downloading a chronicle health record and conduct record of the vehicle driver; and identifying the identified action based on the chronicle health and conduct record.

25. The apparatus of claim 24, wherein the identified action is indicative of switching to a self-driving function, the apparatus comprising:

a self-driving interface, wherein the memory storing computer-executable instructions that when executed by the processor further cause the apparatus to perform:

instructing, through the self-driving interface, the vehicle to be self-driven to an emergency health service.

26. The apparatus of claim 24, wherein the memory storing computer-executable instructions that when executed by the processor further cause the apparatus to perform:

based on the chronicle health and conduct record of the vehicle driver, applying a first weight to the first resultant information about the first biometric feature and a second weight to a second resultant information about a second biometric feature, wherein the first weight and the second weight are different.

27. The apparatus of claim 24, wherein the memory storing computer-executable instructions that when executed by the processor further cause the apparatus to perform:

when the health event is detected, sending the chronicle health and conduct record to an emergency service.

* * * * *

UNITED STATES PATENT AND TRADEMARK OFFICE
CERTIFICATE OF CORRECTION

Page 1 of 2

PATENT NO. : 11,170,899 B2
APPLICATION NO. : 16/797071
DATED : November 9, 2021
INVENTOR(S) : Choi et al.

It is certified that error appears in the above-identified patent and that said Letters Patent is hereby corrected as shown below:

In the Specification

Column 4, Detailed Description, Line 63:
After "model.", delete "¶"

Column 12, Detailed Description, Line 34:
After "condition.", delete "¶"

Column 16, Detailed Description, Line 3:
Delete "$C_{rh}$" and insert --$C_{rb}$--

Column 16, Detailed Description, Line 10:
Delete "$V_t=[B_{rb}, C_{rb},$" and insert --$V_t=[B_{tb}, C_{tb},$--

Column 16, Detailed Description, Lines 10-11:
Delete "$B_{rb}$ and $C_{th}$" and insert --$B_{tb}$ and $C_{tb}$--

Column 16, Detailed Description, Line 12:
Delete ", and $C_{tm}$ are" and insert --is--

Column 16, Detailed Description, Line 13:
Delete "$C_{tm}$" and insert --$C_{tv}$--

Column 16, Detailed Description, Line 20:
After "1005.", delete "¶"

Column 16, Detailed Description, Line 52:
Delete "Bdiff>=Bth, if Ct>Cr," and insert --$B_{diff}>=B_{th}$, if $C_t>C_r$,--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,170,899 B2

Column 16, Detailed Description, Line 53:
Delete "V=[Bt,Ct]." and insert --V=[$B_t,C_t$].--

Column 16, Detailed Description, Line 53:
Delete "V=[Br,Cr]." and insert --V=[$B_r,C_r$].--

Column 17, Detailed Description, Line 2:
Delete "Ci>=$C_{min}$" and insert --$C_i$>=$C_{min}$--

Column 17, Detailed Description, Line 44:
Delete "$V_{tt}$=[23, 0.80, 80," and insert --$V_{t1}$=[23, 0.80, 80,--